United States Patent
Miki et al.

(10) Patent No.: US 7,049,441 B2
(45) Date of Patent: May 23, 2006

(54) PROCESS FOR PREPARATION OF BENZYLPIPERIDINE COMPOUNDS

(75) Inventors: Shokyo Miki, Toyonaka (JP); Mitsuhiro Takeda, Neyagawa (JP); Koji Nakamoto, Yao (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 82 days.

(21) Appl. No.: 10/939,293

(22) Filed: Sep. 10, 2004

(65) Prior Publication Data
US 2005/0038257 A1 Feb. 17, 2005

Related U.S. Application Data

(62) Division of application No. 10/466,494, filed as application No. PCT/JP02/00304 on Jan. 18, 2002, now Pat. No. 6,833,457.

(30) Foreign Application Priority Data
Jan. 18, 2001 (JP) .............................. 2001-10354

(51) Int. Cl.
*C07D 211/70* (2006.01)
(52) U.S. Cl. ...................... 546/233; 546/234
(58) Field of Classification Search ................ 546/233, 546/234
See application file for complete search history.

(56) References Cited

U.S. PATENT DOCUMENTS

| | | |
|---|---|---|
| 4,243,666 A | 1/1981 | Campbell et al. |
| 4,690,931 A | 9/1987 | Wick et al. |
| 4,822,780 A | 4/1989 | Tsuda et al. |

FOREIGN PATENT DOCUMENTS

| | | |
|---|---|---|
| EP | 0 976 722 | 1/1998 |
| JP | 04-312572 | 11/1992 |
| WO | WO 00/61569 | 10/2000 |

OTHER PUBLICATIONS

Zhou, et al., "A Practical Synthesis of 4-(Substituted-benzyl)piperidines and (±)-3-(Substituted-benzyl)pyrrolidines via a Wittig Reaction", *J. Org. Chem* (1999), 64(10): pp. 3763-3766.

*Primary Examiner*—Bernard Dentz
(74) *Attorney, Agent, or Firm*—Elaine M. Ramesh; Mark Chao

(57) ABSTRACT

According to the process as shown in the following scheme having a step for reacting Compound (I) with Compound (II) to produce Compound (III), benzylpiperidine compounds useful as synthesis starting materials of pharmaceutical agents, agricultural chemicals and the like can be produced conveniently by a short step:

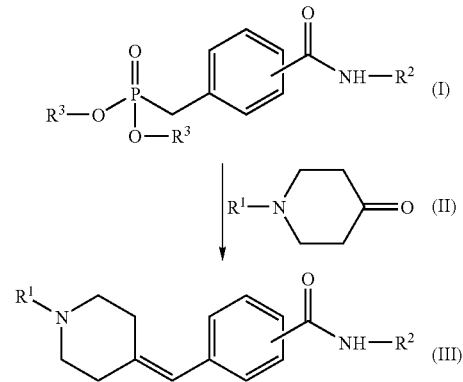

wherein $R^1$ is a hydrogen atom or an amino-protecting group, $R^2$ is a hydrogen atom, a hydrocarbon group optionally having substituents, an alkoxy group optionally having substituents or a heterocyclic group optionally having substituents, and $R^3$ is a lower alkyl group.

13 Claims, No Drawings

PROCESS FOR PREPARATION OF BENZYLPIPERIDINE COMPOUNDS

This application is a divisional of U.S. patent application Ser. No. 10/466,494 filed Jul. 17, 2003, now U.S. Pat. No. 6,833,457, issued Dec. 21, 2004, which was the National Phase filing of International Patent Application No. PCT/JP02/00304, filed Jan. 18, 2002.

TECHNICAL FIELD

The present invention relates to a benzylpiperidine compound useful as a production intermediate for a cyclic amide compound and the like used as a therapeutic agent for acquired immunodeficiency syndrome and a production method thereof.

BACKGROUND ART

As synthetic methods of benzylpiperidine compounds, (i) a method via reduction of carbonyl group (Wolff-Kishner reduction, etc.) after Friedel-Crafts reaction and (ii) a method via olefin synthesis reaction such as Wittig reaction and Horner-Emmons reaction etc. as shown in the following are known.

(i) The method of A. Wick et al. (U.S. Pat. No. 4,690,931, 1987)

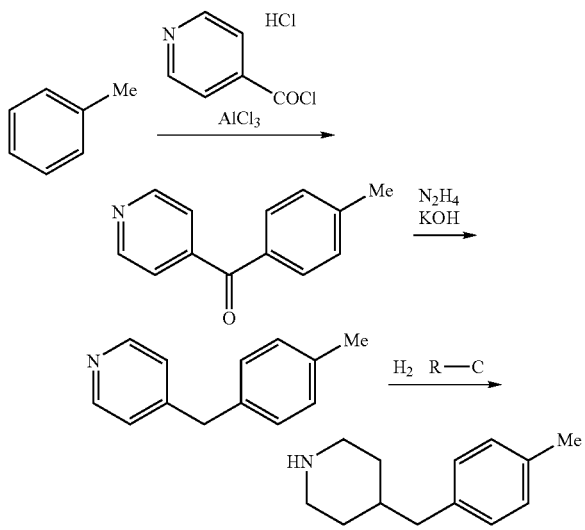

(ii) The paper of Z-L Zhou et al. (*J. Org. Chem.*, 1999, vol. 64, p. 3763)

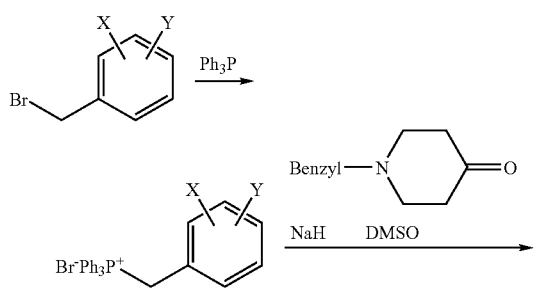

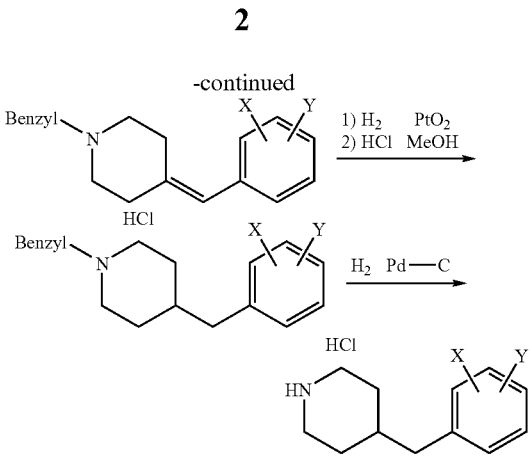

Of the benzylpiperidine compounds, particularly when a compound where a carbamoyl group substitutes on the benzene ring is to be synthesized, a method that goes through an olefin synthesis reactions such as Wittig reaction and the like is advantageous in that the position of substitution can be controlled easily. However, it is not known that benzylpiperidine compounds substituted by a carbamoyl group having an acidic hydrogen disadvantageous to the reaction can be produced through those reactions.

In addition, Takayanagi et al. (WO98/31661) obtained a benzylpiperidine compound substituted by methoxycarbonyl group, and thereafter converted the methoxycarbonyl group to a substituted carbamoyl group.

When this example described in WO98/31661 and an azidation reaction are combined, a carbamoyl-substituted benzylpiperidine compound can be synthesized as shown by the following formulas.

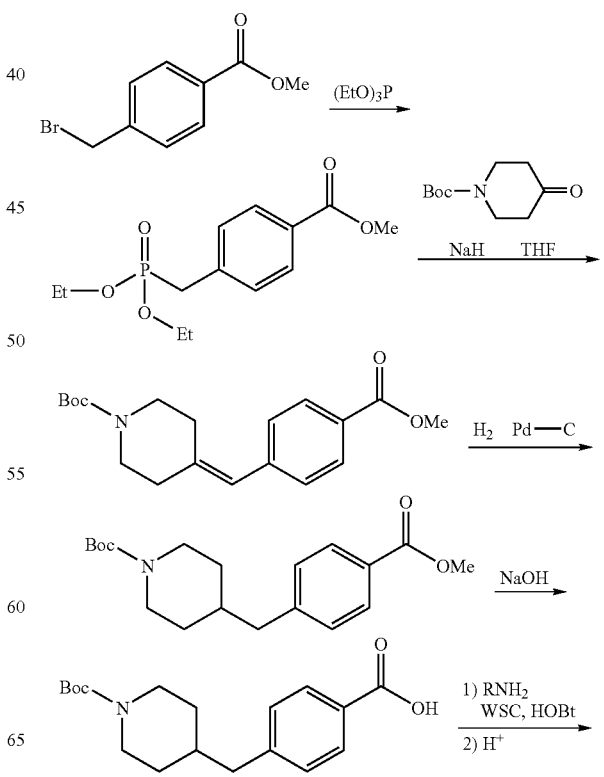

-continued

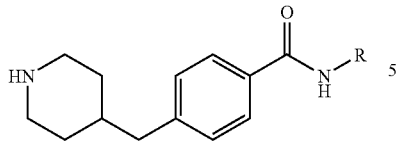

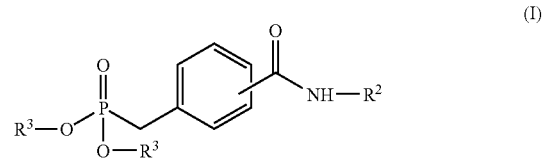

wherein HOBt is hydroxy-1H-benzotriazole and WSC is 1-ethyl-3-(3-dimethylaminopropyl)carbodiimide hydrochloride.

However, the production method is complicated, and the development of an industrially advantageous short-step production method is necessary.

In view of the above, it is an object of the present invention to provide an industrially advantageous short-step production method of a benzylpiperidine compound wherein a carbamoyl group substitutes on the benzene ring, and to provide a novel synthetic intermediate for this production method.

DISCLOSURE OF THE INVENTION

In view of the above-mentioned aspects, the present inventors have conducted intensive studies and, as a result, found that the Horner-Emmons reaction between Compound (I) to be described below, which is substituted by a carbamoyl group having an acidic hydrogen disadvantageous to the reaction, and piperidone Compound (II) to be described below unexpectedly proceeds in a good yield, and the handling property during isolation and purification of product can be markedly improved, and succeeded in synthesizing benzylpiperidine Compound (VIII) to be described below from readily available 4-(chloromethyl)benzoyl chloride by short steps via Compound (I), which resulted in the completion of the present invention.

The present inventors have found a novel production method of Compound (IX) to be described below, which is used for leading the benzylpiperidine Compound (VIII) obtained by the above-mentioned reaction into Compound (X) to be described below, which is useful as a pharmaceutical agent, which resulted in the completion of the present invention.

Accordingly, the present invention relates to the following (1) to (16).

(1) A process for the preparation of a compound represented by the formula:

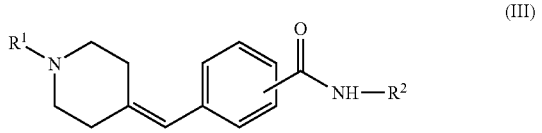

wherein
R$^1$ is a hydrogen atom or an amino-protecting group and
R$^2$ is a hydrogen atom, a hydrocarbon group optionally having substituents, an alkoxy group optionally having substituents or a heterocyclic group optionally having substituents, or a salt thereof, which comprises reacting a compound represented by the formula:

wherein R$^3$ is a lower alkyl group and R$^2$ is as defined above, or a salt thereof, with a compound represented by the formula:

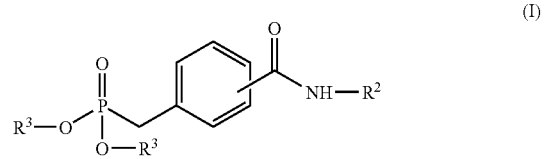

wherein R$^1$ is as defined above, or a salt thereof.

(2) A process for the preparation of a compound represented by the formula:

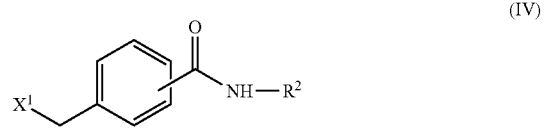

wherein
R$^2$ is a hydrogen atom, a hydrocarbon group optionally having substituents, an alkoxy group optionally having substituents or a heterocyclic group optionally having substituents, and
R$^3$ is a lower alkyl group, or a salt thereof, which comprises reacting a compound represented by the formula:

wherein X$^1$ is a halogen atom and R$^2$ is as defined above, or a salt thereof, with a trialkyl phosphite represented by the formula:

$$(R^3O)_3P \quad (V)$$

wherein R$^3$ is as defined above.

(3) A process for the preparation of a compound represented by the formula:

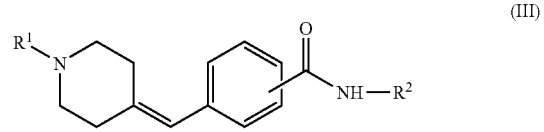

wherein
R$^1$ is a hydrogen atom or an amino-protecting group and
R$^2$ is a hydrogen atom, a hydrocarbon group optionally having substituents, an alkoxy group optionally having substituents or a heterocyclic group optionally having substituents, or a salt thereof, which comprises reacting a compound represented by the formula:

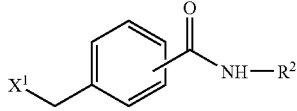

(IV)

wherein $X^1$ is a halogen atom and $R^2$ is as defined above, or a salt thereof, with a trialkyl phosphite represented by the formula:

(V)

wherein $R^3$ is a lower alkyl group, and thereafter reacting with a compound represented by the formula:

(II)

wherein $R^1$ is as defined above, or a salt thereof.

(4) The process of the above-mentioned (3), wherein the compound represented by the formula (IV) or a salt thereof is reacted with the trialkyl phosphite represented by the formula (V) to give a compound represented by the formula:

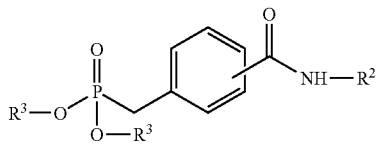

(I)

wherein
$R^2$ is a hydrogen atom, a hydrocarbon group optionally having substituents, an alkoxy group optionally having substituents or a heterocyclic group optionally having substituents, and
$R^3$ is a lower alkyl group, or a salt thereof.

(5) A process for the preparation of a compound represented by the formula:

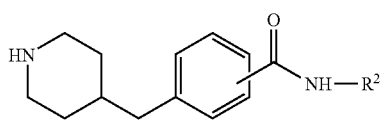

(VIII')

wherein
$R^2$ is a hydrogen atom, a hydrocarbon group optionally having substituents, an alkoxy group optionally having substituents or a heterocyclic group optionally having substituents, or a salt thereof, which comprises:

reacting a compound represented by the formula:

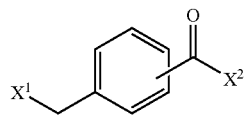

(VI)

wherein $X^1$ is a halogen atom and $X^2$ is a leaving group, with a compound represented by the formula:

$$R^2NH_2$$ (VII)

wherein $R^2$ is as defined above, or a salt thereof, to give a compound represented by the formula:

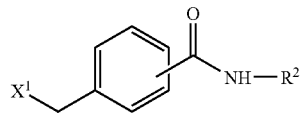

(IV)

wherein $R^2$ and $X^1$ are as defined above, or a salt thereof; reacting the compound represented by the formula (IV) or a salt thereof with a trialkyl phosphite represented by the formula:

(V)

wherein $R^3$ is a lower alkyl group;

thereafter reacting with a compound represented by the formula:

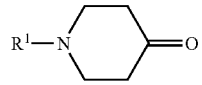

(II)

wherein $R^1$ is a hydrogen atom or an amino-protecting group, or a salt thereof, to give a compound represented by the formula:

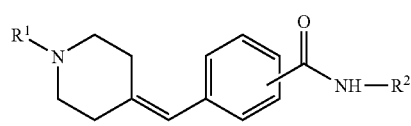

(III)

wherein $R^1$ and $R^2$ are as defined above, or a salt thereof; and reducing and thereafter where necessary deprotecting the compound represented by the formula(III) or a salt thereof.

(6) The process of the above-mentioned (5) which comprises:

reacting a compound represented by the formula:

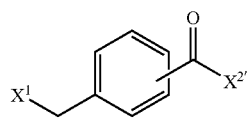

(VI')

wherein $X^1$ and $X^{2'}$ are each a halogen atom, with a compound represented by the formula:

$$R^2NH_2 \qquad (VII)$$

wherein $R^2$ is a hydrogen atom, a hydrocarbon group optionally having substituents, an alkoxy group optionally having substituents or a heterocyclic group optionally having substituents, or a salt thereof, to give a compound represented by the formula:

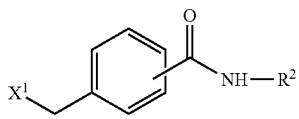
(IV)

wherein $R^2$ and $X^1$ are as defined above, or a salt thereof; reacting the compound represented by the formula (IV) or a salt thereof with a trialkyl phosphite represented by the formula:

$$(R^3O)_3P \qquad (V)$$

wherein $R^3$ is a lower alkyl group, to give a compound represented by the formula:

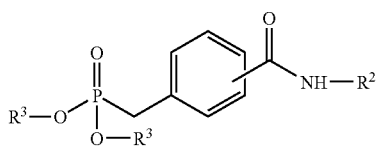
(I)

wherein $R^2$ and $R^3$ are as defined above, or a salt thereof; reacting the compound represented by the formula (I) or a salt thereof with a compound represented by the formula:

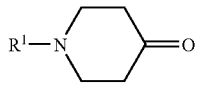
(II)

wherein $R^1$ is a hydrogen atom or an amino-protecting group, or a salt thereof, to give a compound represented by the formula:

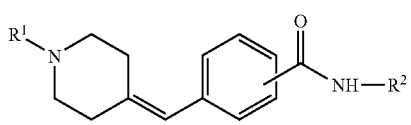
(III)

wherein $R^1$ and $R^2$ are as defined above, or a salt thereof; and reducing and thereafter where necessary deprotecting the compound represented by formula (III) or a salt thereof.

(7) A process for the preparation of a compound represented by the formula:

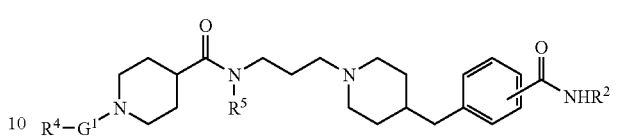
(X)

wherein $G^1$ is a bond, CO or $SO_2$, $R^2$ is a hydrogen atom, a hydrocarbon group optionally having substituents, an alkoxy group optionally having substituents or a heterocyclic group optionally having substituents, $R^4$ is a hydrogen atom, a hydrocarbon group optionally having substituents, a heterocyclic group optionally having substituents, an alkoxy group optionally having substituents, an aryloxy group optionally having substituents or an amino group optionally having substituents, and $R^5$ is a cyclic hydrocarbon group optionally having substituents or a heterocyclic group optionally having substituents, which comprises:
reacting a compound represented by the formula:

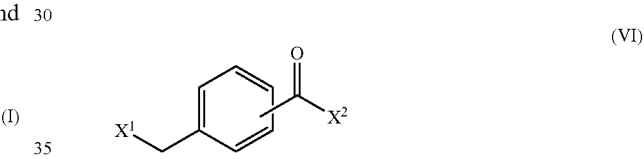
(VI)

wherein $X^1$ is a halogen atom and $X^2$ is a leaving group, with a compound represented by the formula:

$$R^2NH_2 \qquad (VII)$$

wherein $R^2$ is as defined above, or a salt thereof, to give a compound represented by the formula:

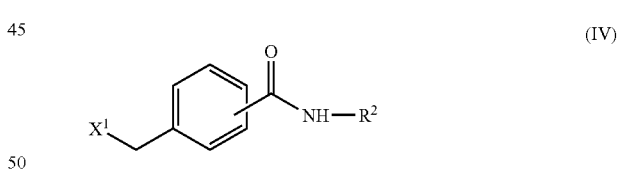
(IV)

wherein $R^2$ and $X^1$ are as defined above, or a salt thereof; reacting the compound represented by the formula (IV) or a salt thereof with a trialkyl phosphite represented by the formula:

$$(R^3O)_3P \qquad (V)$$

wherein $R^3$ is a lower alkyl group;

thereafter reacting with a compound represented by the formula:

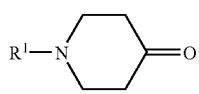
(II)

wherein $R^1$ is a hydrogen atom or an amino-protecting group, or a salt thereof, to give a compound represented by the formula:

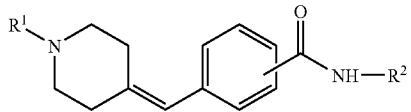
(III)

wherein $R^1$ and $R^2$ are as defined above, or a salt thereof; reducing and thereafter where necessary deprotecting the compound represented by the formula (III) or a salt thereof to give a compound represented by the formula:

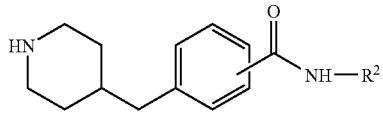
(VIII')

wherein $R^2$ is as defined above, or a salt thereof; and reacting the compound represented by the formula (VIII') or a salt thereof with a compound represented by the formula:

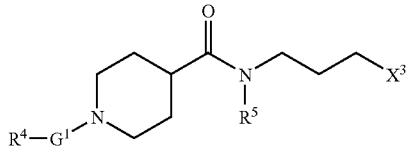
(IX)

wherein $X^3$ is a leaving group and $G^1$, $R^4$ and $R^5$ are as defined above, or a salt thereof.

(8) The process of any of the above-mentioned (2) to (7), wherein the compound represented by the formula (IV) or a salt thereof is reacted with the compound represented by the formula (V) in the presence of alkali metal iodide.

(9) The process of the above-mentioned (8), wherein the alkali metal iodide is potassium iodide.

(10) The process of the above-mentioned (1), (3), (4), (5), (6) or (7), wherein the compound represented by the formula (II) or a salt thereof is reacted in the presence of a base.

(11) The process of the above-mentioned (10), wherein the base is t-butoxide of an alkali metal.

(12) The process of the above-mentioned (11), wherein the base is potassium t-butoxide.

(13) A process for the preparation of a compound represented by the formula:

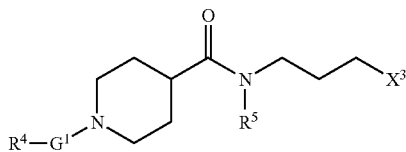
(IX)

wherein
$G^1$ is a bond, CO or $SO_2$,
$X^3$ is a leaving group,
$R^4$ is a hydrogen atom, a hydrocarbon group optionally having substituents, a heterocyclic group optionally having substituents, an alkoxy group optionally having substituents, an aryloxy group optionally having substituents or an amino group optionally having substituents, and
$R^5$ is a cyclic hydrocarbon group optionally having substituents or a heterocyclic group optionally having substituents, or a salt thereof, which comprises reacting a compound represented by the formula:

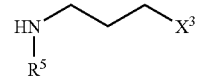
(XI)

wherein $X^3$ and $R^5$ are as defined above, or a salt thereof, with a compound represented by the formula:

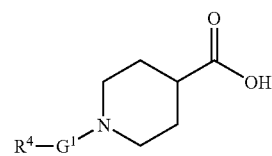
(XII)

wherein $G^1$ and $R^4$ are as defined above, or a salt thereof.

(14) A process for the preparation of a compound represented by the formula:

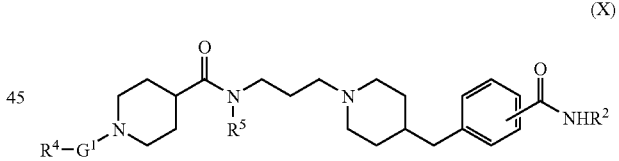
(X)

wherein
$G^1$ is a bond, CO or $SO_2$,
$R^2$ is a hydrogen atom, a hydrocarbon group optionally having substituents, an alkoxy group optionally having substituents or a heterocyclic group optionally having substituents,
$R^4$ is a hydrogen atom, a hydrocarbon group optionally having substituents, a heterocyclic group optionally having substituents, an alkoxy group optionally having substituents, an aryloxy group optionally having substituents or an amino group optionally having substituents, and
$R^5$ is a cyclic hydrocarbon group optionally having substituents or a heterocyclic group optionally having substituents, or a salt thereof, which comprises reacting a compound represented by the formula:

(XI)

wherein $X^3$ is a leaving group and $R^5$ is as defined above, or a salt thereof, with a compound represented by the formula:

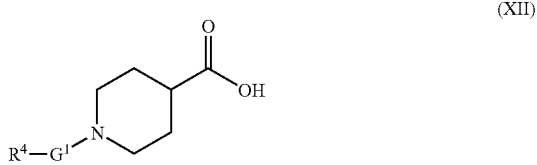

(XII)

wherein $G^1$ and $R^4$ are as defined above, or a salt thereof, to give a compound represented by the formula:

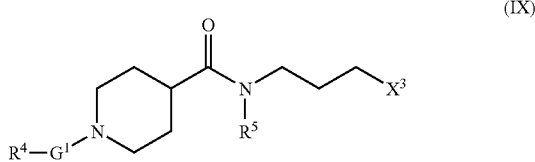

(IX)

wherein $G^1$, $X^3$, $R^4$ and $R^5$ are as defined above, or a salt thereof, and reacting the compound represented by the formula (IX) or a salt thereof with a compound represented by the formula:

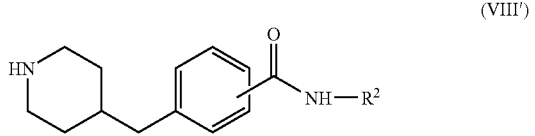

(VIII')

wherein $R^2$ is as defined above, or a salt thereof.

(15) The process of the above-mentioned (14), wherein $R^2$ is a hydrogen atom, $R^4$ is a methyl group, $R^5$ is a phenyl group having 1 or 2 substituents selected from the group consisting of a halogen atom and a methyl group, $G^1$ is a carbonyl, and $X^3$ is a chlorine atom.

(16) A compound represented by the formula:

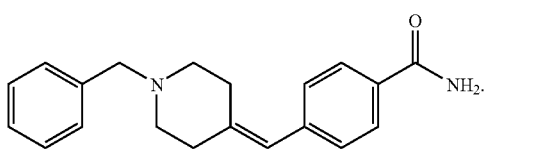

(III')

As the 'halogen atom' denoted by the above-mentioned $X^1$ and $X^{2'}$, for example, chlorine atom, bromine atom, iodine atom and the like can be mentioned.

As the 'leaving group' denoted by $X^2$, for example, a halogen atom (e.g., chlorine atom, bromine atom, iodine atom, etc.), an alkyl or arylsulfonyloxy group (e.g., methanesulfonyloxy, ethanesulfonyloxy, benzenesulfonyloxy, p-toluenesulfonyloxy, etc.) and the like can be mentioned.

As the 'amino-protecting group' denoted by $R^1$, any protecting group can be used as long as it does not inhibit the reaction, and carbamate protecting groups (e.g., benzyloxycarbonyl group, t-butoxycarbonyl group, etc.), amide protecting groups (e.g., formyl group, etc.), aminoacetal protecting groups (e.g., benzyloxymethyl group, etc.), benzyl protecting groups (e.g., benzyl group, etc.) and the like are preferably used. Of these, benzyl group, benzyloxycarbonyl group and t-butoxycarbonyl group are particularly preferable.

As the 'hydrocarbon group' of the 'hydrocarbon group optionally having substituents' denoted by $R^2$, lower alkyl groups (e.g., $C_{1-6}$ alkyl group such as methyl, ethyl, propyl, isopropyl, butyl, isobutyl, t-butyl, pentyl, hexyl etc. and the like), cycloalkyl groups (e.g., $C_{3-6}$ cycloalkyl group such as cyclopropyl, cyclobutyl, cyclopentyl, cyclohexyl etc. and the like), aryl groups (e.g., $C_{6-10}$ aryl group such as phenyl, 1-naphthyl, 2-naphthyl etc. and the like), aralkyl groups (e.g., $C_{7-10}$ aralkyl group such as benzyl, phenethyl and the like, preferably phenyl-$C_{1-4}$ alkyl group, etc.), and the like can be mentioned.

As the 'alkoxy group' of the 'alkoxy group optionally having substituents' denoted by $R^2$, for example, $C_{1-6}$ alkoxy groups such as methoxy, ethoxy, n-propoxy, isopropoxy, n-butoxy, isobutoxy, sec-butoxy, t-butoxy and the like, and the like can be mentioned.

As the 'heterocyclic group' of the 'heterocyclic group optionally having substituents' denoted by $R^2$, aromatic heterocyclic groups and saturated or unsaturated non-aromatic heterocyclic groups, containing, as an atom constituting the ring system (ring atom), at least one of 1 to 3 kinds of hetero atoms, which is selected from oxygen atom, sulfur atom, nitrogen atom and the like, can be mentioned. As the aromatic heterocyclic group, for example, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, benzofuranyl, isobenzofuranyl, benzothienyl, indolyl, isoindolyl, 1H-indazolyl, benzindazolyl, benzoxazolyl, 1,2-benzisoxazolyl, benzothiazolyl, benzopyranyl, 1,2-benzisothiazolyl, benzodioxolyl, benzimidazolyl, 2,1,1-benzoxadiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenathridinyl, phenathrolinyl, indolizinyl, pyrrolo[1,2-b]pyridazinyl, pyrazolo[1,5-a]pyridyl, pyrazolo[3,4-b]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like can be mentioned, and as the saturated or unsaturated non-aromatic heterocyclic groups, for example, oxiranyl, azetidinyl, oxetanyl, thietanyl, pyrrolidinyl, tetrahydrofuryl, thiolanyl, piperidinyl, tetrahydropyranyl, morpholinyl, thiomorpholinyl and piperazinyl and the like can be mentioned.

As the 'substituent' of the 'hydrocarbon group optionally having substituents', 'alkoxy group optionally having substituents' and 'heterocyclic group optionally having substituents', for example, (1) hydroxyl group, (2) amino group, (3) mono- or di-substituted amino group [e.g., mono- or di-substituted amino group substituted by 1 or 2 substituents selected from $C_{1-6}$ alkyl group (methyl, ethyl, n-propyl, isopropyl, n-butyl, t-butyl, n-pentyl, n-hexyl), $C_{1-6}$ alkanoyl (e.g., acetyl, propionyl, butyryl, etc.), $C_{7-13}$ arylcarbonyl (e.g., benzoyl, naphthoyl, etc.) and $C_{1-6}$ alkylsulfonyl (methylsulfonyl, ethylsulfonyl, propylsulfonyl, butylsulfonyl, pentylsulfonyl, etc.)], (4) halogen atom (e.g., fluorine, chlorine, bromine, iodine, etc.), (5) nitro group, (6) cyano group, (7) $C_{1-6}$ alkyl group (methyl, ethyl, n-propyl, isopropyl, n-butyl, t-butyl, n-pentyl, n-hexyl, etc.) optionally substituted by halogen atom (e.g., fluorine, chlorine, bromine, iodine, etc.) or (8) $C_{1-6}$ alkoxy group (e.g., methoxy, ethoxy, n-propoxy, isopropoxy, n-butoxy, t-butoxy, n-pentyloxy, n-hexyloxy, etc.) optionally substituted by halogen atom (e.g., fluorine, chlorine, bromine, iodine, etc.), and the like can be mentioned.

As the $R^2$, $C_{1-2}$ alkyl such as methyl, ethyl and the like and a hydrogen atom are preferable.

As the lower alkyl group denoted by $R^3$, for example, those having 1 to 4 carbon atoms, such as methyl, ethyl, n-propyl, isopropyl and the like, can be mentioned, with preference given to methyl and ethyl.

The production methods of the present invention are explained in the following.

Production of Compound (III)

A compound represented by the formula (III) or a salt thereof can be produced by reacting a compound represented by the formula (I) or a salt thereof with a piperidone compound of the formula (II) or a salt thereof.

When —$NHR^2$ of the compound of the formula (I) has a basic group such as an amino group and the like, an acid addition salt, for example, a salt such as inorganic acid salts (e.g., hydrochloride, sulfate, hydrobromide, phosphate, etc.), organic acid salts (e.g., acetate, trifluoroacetate, succinate, maleate, fumarate, propionate, citrate, tartrate, lactate, oxalate, methanesulfonate, p-toluenesulfonate, etc.) and the like can be formed. As the salt of the compound of the formula (I), these salts can be used.

In the following, a compound represented by the formula (I) and a salt thereof are simply referred to as Compound (I). In addition, the compounds represented by the formula (II) and the formula (III) can form a salt, and as such salt, those similar to the salts of the compound of the above-mentioned formula (I) can be mentioned. In the following, the compound represented by the formula (II) and a salt thereof are simply referred to as Compound (II), and the compound represented by the formula (III) and a salt thereof are simply referred to as Compound (III). Compound (III), wherein $R^1$ is a benzyl group, $R^2$ is a hydrogen atom, and the carbamoyl group is linked to the para-position, and a salt thereof, is novel (a compound represented by the aforementioned formula (III') and a salt thereof, which are hereinafter simply referred to as Compound (III')).

The reaction between Compound (I) and Compound (II) is generally carried out in a solvent in the presence of a base. As the solvent, any solvent can be used as long as the reaction is not inhibited. For example, amides (e.g., N,N-dimethylformamide, N,N-dimethylacetamide, N-methylpyrrolidone, etc.) and nitriles (e.g., acetonitrile, etc.) are preferably used. These solvents can be used alone or as a mixture of two or more kinds thereof.

As the base, for example, alkali metal alkoxides having 1 to 4 carbon atoms such as t-butoxide of alkali metal (e.g., potassium t-butoxide, sodium t-butoxide), sodium methoxide, sodium ethoxide and the like can be mentioned. Of these, t-butoxide of alkali metal is preferable, and potassium t-butoxide is particularly preferable.

The Compound (II) is used in an amount of generally 0.5 mole to 5 moles, preferably 0.8 mole to 3 moles, per 1 mole of Compound (I). The amount of the base to be used is generally 1 mole to 10 moles, preferably 1 mole to 3 moles, per 1 mole of Compound (I).

The reaction temperature is generally −20° C. to 150° C., preferably 0° C. to 50° C., and the reaction time is generally 10 min. to 12 hrs., preferably 30 min. to 5 hrs.

Production of Compound (I)

The Compound (I) can be produced by reacting a compound represented by the formula (IV) or a salt thereof with a compound represented by the formula (V) [hereinafter to be referred to as Compound (V)]. The compound represented by the formula (IV) can form a salt and as such salt, those similar to the salt of the compound represented by the above-mentioned formula (I) can be mentioned. In the following, a compound represented by the formula (IV) and a salt thereof are simply referred to as Compound (IV).

The reaction between Compound (IV) and Compound (V) is carried out generally in the presence of a solvent and as such solvent, any solvent can be used as long as it does not inhibit the reaction. For example, amides (e.g., N,N-dimethylformamide, N,N-dimethylacetamide, N-methylpyrrolidone, etc.), nitriles (e.g., acetonitrile, etc.), and alcohols (e.g., methanol, ethanol, propanol, etc.) are preferably used. These solvents can be used alone or in a mixture of two or more kinds thereof.

The Compound (V) is used in an amount of generally 1 mole to 10 moles, preferably 1 mole to 5 moles, per 1 mole of Compound (IV). To promote this reaction, for example, an alkali metal iodide such as potassium iodide, sodium iodide and the like is desirably used concurrently. Of these, potassium iodide is particularly preferably used concurrently. Said alkali metal iodide is used in an amount of generally 0.1 mole to 5 moles, preferably 0.5 mole to 3 moles, per 1 mole of Compound (IV).

This reaction is generally carried out at a reaction temperature of 20° C. to 150° C., preferably 50° C. to 100° C., generally for 30 min. to 24 hrs., preferably 1 hr. to 5 hrs. The phosphonic acid ester (Compound (I)) obtained by this reaction may be isolated, but may be conveniently applied to the subsequent Horner-Emmons reaction with Compound (II) as it is or after evaporation of the solvent. When Compound (I) is applied for the production of the above-mentioned Compound (III) without isolation, the reagents to be used may be used in an amount within the above-mentioned range, while assuming that Compound (I) has been obtained quantitatively from Compound (IV).

Production of Compound (IV)

The Compound (IV) can be produced by reacting a compound represented by the formula (VI) [hereinafter to be referred to as Compound (VI), and a compound represented by the formula (VI'), which is a Compound (VI) wherein $X^2$ is a halogen atom, and a salt thereof are hereinafter to be simply referred to as Compound (VI')] with an amine compound represented by the formula (VII) or a salt thereof. The compound represented by the formula (VII) can form a salt and as such salt, those similar to the salt of the compound represented by the above-mentioned formula (I) can be mentioned. In the following, a compound represented by the formula (VII) and a salt thereof are simply referred to as Compound (VII).

This reaction is generally carried out in a solvent and as such solvent, any solvent can be used as long as it does not inhibit the reaction. For example, hydrocarbons (e.g., n-hexane, n-heptane, benzene, toluene, xylene, etc.), halogenated hydrocarbons (e.g., dichloromethane, etc.), ethers (e.g., diethyl ether, diisopropyl ether, ethylene glycol dimethyl ether, tetrahydrofuran, dioxane, etc.), amides (e.g., N,N-dimethylformamide, N,N-dimethylacetamide, N-methylpyrrolidone, etc.), esters (e.g., ethyl acetate, methyl acetate, etc.), nitrites (e.g., acetonitrile, etc.), sulfoxides (e.g., dimethyl sulfoxide, etc.), ketones (e.g., acetone, 2-butanone, 4-methyl-2-pentanone, cyclohexanone, etc.), alcohols (e.g., methanol, ethanol, propanol, etc.), water and the like can be included. Of these, hydrocarbons (e.g., n-hexane, n-heptane, benzene, toluene, xylene, etc.), ethers (e.g., diethyl ether, diisopropyl ether, ethylene glycol dimethyl ether, tetrahydrofuran, dioxane, etc.), amides (e.g., N,N-dimethylformamide, N,N-dimethylacetamide, N-methylpyrrolidone, etc.), esters (e.g., ethyl acetate, methyl acetate, etc.), nitriles (e.g., acetonitrile, etc.), and ketones (e.g., acetone, 2-butanone, 4-methyl-2-pentanone, cyclohexanone, etc.) are preferable. These solvents can be used alone or in a mixture of two or more kinds thereof.

The amount of the Compound (VII) to be used is generally 1 mole to 30 moles, preferably 1 mole to 10 moles, per 1 mole of Compound (VI). Compound (VII) may be used in an aqueous solution.

In this reaction, a base may be present to control the reaction speed, dissolution property and the like. As the base, for example, sodium hydroxide, potassium hydroxide, sodium hydrogencarbonate, sodium carbonate, potassium carbonate, potassium t-butoxide, triethylamine, diisopropylethylamine, pyridine, dimethylaminopyridine, 1,8-diazabicyclo[5,4,0]-7-undecene and the like are preferable. The base is used generally in an amount of 1 mole to 100 moles, preferably 1 mole to 30 moles, per 1 mole of Compound (VI) and may be used in an aqueous solution.

This reaction is carried out generally at a reaction temperature of −20° C. to 150° C., preferably 0° C. to 50° C., for generally 10 min. to 12 hrs., preferably 1 hr. to 3 hrs.

Compound (VI) can be easily available as a commercial product. Compound (IV) is also commercial available.

Production of Compound (VIII)

By reduction of Compound (III), a compound represented by the formula:

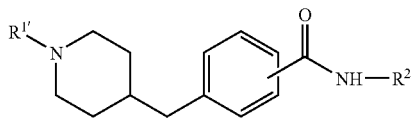

(VIII)

wherein $R^{1'}$ is a hydrogen atom or an amino-protecting group, and $R^2$ is a hydrogen atom, a hydrocarbon group optionally having substituents, an alkoxy group optionally having substituents or a heterocyclic group optionally having substituents, or a salt thereof can be obtained, which is deprotected as necessary to give Compound (VIII'). As the amino-protecting group for $R^{1'}$, those similar to the amino-protecting group for $R^1$ can be mentioned. The compound represented by the formula (VIII) can form a salt, and as such salt, those similar to the salt of the compound represented by the above-mentioned formula (I) can be mentioned. In the following, a compound represented by the formula (VIII) and a salt thereof are simply referred to as Compound (VIII). In Compound (VIII), a compound wherein $R^{1'}$ is a hydrogen atom and a salt thereof (a compound represented by the aforementioned formula (VIII') and a salt thereof) are hereinafter simply referred to as Compound (VIII').

The reduction of Compound (III) is generally conducted in a solvent and as such solvent, any solvent can be used as long as it does not inhibit the reaction. For example, alcohols (e.g., methanol, ethanol, propanol, etc.) and ethers (e.g., tetrahydrofuran, etc.) are preferably used. These may be used alone or in a mixture of two or more kinds thereof. In addition, hydrogen chloride, acetic acid and the like may be used together with these solvents.

For this reduction, hydrogenation reaction is generally preferably used and, for example, palladium carbon, platinum carbon, platinum oxide and the like are used as a catalyst. The catalyst is generally used in an amount of 0.1 wt % to 100 wt %, preferably 0.5 wt % to 50 wt %, of the weight of Compound (III). The hydrogen pressure is preferably approximately 0.1 MPa to 10 MPa, which may be an open system.

This reaction is generally carried out at 0° C. to 100° C., preferably 20° C. to 70° C., for 1 to 12 hrs., preferably 30 min. to 5 hrs.

By the reduction of Compound (III) wherein $R^1$ is an amino-protecting group, Compound (VIII) wherein $R^{1'}$ is an amino-protecting group and the same as $R^1$ can be obtained. When a compound of the formula (III) wherein $R^1$ is an amino-protecting group is used, the protected amino group for $R^1$ may be simultaneously deprotected depending on the means of reduction to give Compound (VIII) wherein $R^{1'}$ is a hydrogen atom, i.e., Compound (VIII'). For example, when a compound wherein $R^1$ is benzyl or N-benzyloxycarbonyl is used as Compound (III), and reduction is conducted using palladium carbon as a catalyst, deprotection takes place simultaneously with the reduction, whereby Compound (VIII) wherein $R^{1'}$ is a hydrogen atom, i.e., Compound (VIII') can be obtained. When a compound wherein $R^1$ is t-butoxycarbonyl is used as Compound (III), and when platinum carbon or platinum oxide is used as a catalyst, Compound (VIII) wherein $R^{1'}$ is the same as $R^1$ can be obtained.

When a compound wherein $R^{1'}$ is a hydrogen atom, namely, Compound (VIII'), is to be produced as Compound (VIII), the compound can be obtained by deprotection after reduction of Compound (III). This deprotection can be generally carried out under, for example, hydrolysis conditions using an aqueous solution of mineral acid such as hydrochloric acid, sulfuric acid and the like, and the like. That is, by reaction using 1 equivalent to 100 equivalents of an acid relative to Compound (III) at 0° C. to 100° C. for 1 to 12 hrs., deprotection is conveniently conducted.

Any compound used for the above-mentioned methods or any compound obtained thereby, and salts thereof can be converted to each other by a method known per se or a method analogous thereto.

Compound (VIII) that can be obtained by the above-mentioned methods is, for example, reacted with a compound represented by the formula:

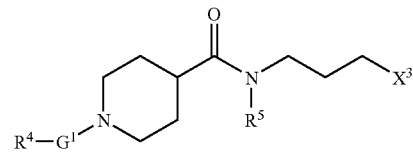

(IX)

wherein $G^1$ is a bond, CO or $SO_2$, $X^3$ is a leaving group, $R^4$ is a hydrogen atom, a hydrocarbon group optionally having substituents, a heterocyclic group optionally having substituents, an alkoxy group optionally having substituents, an aryloxy group optionally having substituents or an amino group optionally having substituents, and $R^5$ is a cyclic hydrocarbon group optionally having substituents or a heterocyclic group optionally having substituents, or a salt thereof to give a compound represented by the formula:

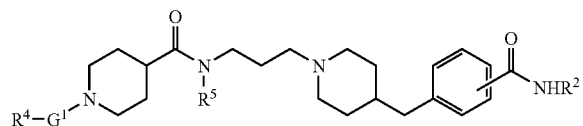

(X)

wherein each symbol is as defined above, or a salt thereof, which is useful as a therapeutic agent of acquired immunodeficiency syndrome.

As the 'leaving group' denoted by $X^3$, for example, halogen atoms (e.g., chlorine atom, bromine atom, iodine atom, etc.), alkyl or arylsulfonyloxy groups (e.g., methanesulfonyloxy, ethanesulfonyloxy, benzenesulfonyloxy, p-toluenesulfonyloxy, etc.) and the like can be mentioned. Of these, chlorine atom is particularly preferable.

As the 'hydrocarbon group' of the 'hydrocarbon group optionally having substituents' denoted by $R^4$, for example, chain aliphatic hydrocarbon group, alicyclic hydrocarbon group, aryl group and the like can be mentioned. Preferred are chain aliphatic hydrocarbon group and alicyclic hydrocarbon group.

As the chain aliphatic hydrocarbon group, for example, linear or branched chain aliphatic hydrocarbon groups such as alkyl group, alkenyl group, alkynyl group and the like can be mentioned, with preference given to alkyl group. As the alkyl group, for example, $C_{1-10}$ alkyl groups (preferably $C_{1-6}$ alkyl, etc.) such as methyl, ethyl, n-propyl, isopropyl, n-butyl, isobutyl, sec-butyl, t-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, n-heptyl, 1-methylheptyl, 1-ethylhexyl, n-octyl, 1-methylheptyl, nonyl and the like, and the like can be mentioned. As the alkenyl group, for example, $C_{2-6}$ alkenyl groups such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like, and the like can be mentioned. As the alkynyl group, for example, $C_{2-6}$ alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like can be mentioned.

As the alicyclic hydrocarbon group, for example, saturated or unsaturated alicyclic hydrocarbon groups such as cycloalkyl group, cycloalkenyl group, cycloalkanedienyl group and the like can be mentioned, with preference given to cycloalkyl group. As the cycloalkyl group, for example, $C_{3-9}$ cycloalkyl (preferably $C_{3-8}$ cycloalkyl, etc.) such as cyclopropyl, cyclobutyl, cyclopentyl, cyclohexyl, cycloheptyl, cyclooctyl, cyclononyl and the like, and fused rings such as 1-indanyl, 2-indanyl and the like can be mentioned. As the cycloalkenyl group, for example, $C_{3-6}$ cycloalkenyl groups such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl and the like, and the like can be mentioned. As the cycloalkanedienyl group, for example, $C_{4-6}$ cycloalkadienyl groups such as 2,4-cyclopentadien-1-yl, 2,4-cyclohexadien-1-yl, 2,5-cyclohexadien-1-yl and the like, and the like can be mentioned.

As the aryl group, monocyclic or condensed polycyclic aromatic hydrocarbon groups can be mentioned. For example, $C_{6-14}$ aryl groups such as phenyl, naphthyl (e.g., 1-naphthyl, 2-naphthyl), anthryl, phenanthryl, acenaphthylenyl, indanyl (e.g., 4-indanyl, 5-indanyl) and the like, and the like are preferable, and phenyl, 1-naphthyl, 2-naphthyl and the like are particularly preferable.

As the 'substituent' of the 'hydrocarbon group optionally having substituents' denoted by $R^4$, for example, optionally substituted alkyl group, optionally substituted alkenyl group, optionally substituted alkynyl group, optionally substituted aryl group, optionally substituted cycloalkyl group, optionally substituted cycloalkenyl group, optionally substituted heterocyclic group, optionally substituted amino group, optionally substituted imidoyl group, optionally substituted amidino group, optionally substituted hydroxyl group, optionally substituted thiol group, optionally esterified carboxyl group, optionally substituted carbamoyl group, optionally substituted thiocarbamoyl group, optionally substituted sulfamoyl group, halogen atoms (e.g., fluorine, chlorine, bromine, iodine and the like, preferably chlorine, bromine, etc.), cyano group, nitro group, sulfonic acid-derived acyl group, carboxylic acid-derived acyl group, optionally substituted alkylsulfinyl group, optionally substituted arylsulfinyl group and the like can be mentioned, wherein 1 to 0.5 (preferably 1 to 3) of these optional substituents may substitute at substitutable positions.

As the aryl group of the 'optionally substituted aryl group' as the substituent, for example, $C_{6-14}$ aryl groups such as phenyl, naphthyl, anthryl, phenanthryl, acenaphthylenyl and the like, and the like can be mentioned. As used herein, as the substituent of the aryl group, lower alkoxy group optionally substituted by halogen (e.g., $C_{1-6}$ alkoxy group such as methoxy, ethoxy, propoxy and the like, halogen-substituted $C_{1-4}$ alkoxy group such as fluoromethoxy, difluoromethoxy, trifluoromethoxy, 1,1-difluoroethoxy, 2,2-difluoroethoxy, 3,3-difluoropropoxy, 2,2,3,3,3-pentafluoropropoxy and the like, etc.), aryloxy optionally having substituents (e.g., phenoxy, 4-fluorophenoxy, 2-carbamoylphenoxy, etc.), halogen atoms (e.g., fluorine, chlorine, bromine, iodine, etc.), lower alkyl groups optionally having substituents (e.g., unsubstituted $C_{1-6}$ alkyl groups such as methyl, ethyl, propyl and the like, halogen-substituted $C_{1-4}$ alkyl group such as fluoromethyl, difluoromethyl, trifluoromethyl, 1,1-difluoroethyl, 2,2-difluoroethyl, 3,3-difluoropropyl, 2,2,3,3,3-pentafluoropropyl and the like, etc.), $C_{3-8}$ cycloalkyl (e.g., cyclopropyl, cyclobutyl, cyclopentyl, cyclohexyl, cycloheptyl, etc.), amino group, mono-substituted amino (e.g., carbamoylamino, methylsulfonylamino, methylamino, ethylamino, propylamino, etc.), di-substituted amino (e.g., dimethylamino, diethylamino, N-methyl-N-methylsulfonylamino, di(methylsulfonyl)amino, etc.), carbamoyl group optionally substituted by $C_{1-6}$ alkyl (e.g., butylcarbamoyl, etc.), formyl, $C_{2-6}$ alkanoyl group (e.g., acetyl, propionyl, butyryl and the like), $C_{6-14}$ aryl group (e.g., phenyl, naphthyl, etc.), $C_{6-14}$ aryl-carbonyl (e.g., benzoyl, naphthoyl, etc.), $C_{7-13}$ aralkyl-carbonyl (e.g., benzylcarbonyl, naphthylmethylcarbonyl, etc.), hydroxyl group, alkanoyloxy (e.g., $C_{2-5}$ alkanoyloxy such as acetyloxy, propionyloxy, butyryloxy and the like), $C_{7-13}$ aralkyl-carbonyloxy (e.g., benzylcarbonyloxy, etc.), nitro group, optionally substituted sulfamoyl group (unsubstituted sulfamoyl group, N-methylsulfamoyl, etc.), optionally substituted arylthio group (e.g., phenylthio, 4-methylphenylthio, etc.), —N~N-phenyl, cyano group, amidino group, optionally esterified carboxyl group (free carboxyl group, $C_{1-4}$ alkoxy-carbonyl such as methoxycarbonyl, ethoxycarbonyl, t-butoxycarbonyl and the like, etc.), $C_{1-6}$ alkylthio, $C_{1-6}$ alkylsulfinyl, $C_{1-6}$ alkylsulfonyl, $C_{6-14}$ arylthio, $C_{6-14}$ arylsulfinyl, $C_{6-14}$ arylsulfonyl, heterocyclic group optionally having substituents (e.g., pyridyl, thienyl, tetrazolyl, morpholinyl, oxazolyl and the like, as well as those recited as the 'heterocyclic group optionally having substituents' denoted by $R^5$ in the following) and the like can be mentioned. One or two of these optional substituents may substitute at substitutable positions.

As the cycloalkyl group of the 'optionally substituted cycloalkyl group' as the substituent, for example, $C_{3-7}$ cycloalkyl groups such as cyclopropyl, cyclobutyl, cyclopentyl, cyclohexyl, cycloheptyl and the like, and the like can be mentioned. Here, as the substituent of the cycloalkyl group, a similar number of those similar to the substituent of the aforementioned 'optionally substituted aryl group' can be mentioned.

As the cycloalkenyl group of the 'optionally substituted cycloalkenyl group' as the substituent, for example, $C_{3-6}$ cycloalkenyl groups such as cyclopropenyl, cyclobutenyl, cyclopentenyl, cyclohexenyl and the like, and the like can be mentioned. Here, as the substituent of the optionally substituted cycloalkenyl group, a similar number of those similar to the substituent of the aforementioned 'optionally substituted aryl group' can be mentioned.

As the alkyl group of the 'optionally substituted alkyl group' as a substituent, for example, $C_{1-6}$ alkyl such as methyl, ethyl, n-propyl, isopropyl, n-butyl, isobutyl, sec-butyl, t-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl and the like, and the like can be mentioned. Here, as the substituent of the alkyl group, a similar number of those similar to the substituent of the aforementioned 'optionally substituted aryl group' can be mentioned.

As the alkenyl group of the 'optionally substituted alkenyl group' as a substituent, for example, $C_{2-6}$ alkenyl group such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like, and the like can be mentioned. Here, as the substituent of the alkenyl group, a similar number of those similar to the substituent of the aforementioned 'optionally substituted aryl group' can be mentioned.

As the alkynyl group of the 'optionally substituted alkynyl group' as a substituent, for example, $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like can be mentioned. Here, as the substituent of the alkynyl group, a similar number of those similar to the substituent of the aforementioned 'optionally substituted aryl group' can be mentioned.

As the heterocyclic group of the 'optionally substituted heterocyclic group' as a substituent, an aromatic heterocyclic group, a saturated or unsaturated non-aromatic heterocyclic group (aliphatic heterocyclic group) and the like, which contain, as an atom constituting the ring (ring atom), at least one (preferably 1 to 4, more preferably 1 or 2) of 1 to 3 kinds (preferably 1 or 2 kinds) of hetero atoms, which is selected from oxygen atom, sulfur atom and nitrogen atom, and the like can be mentioned.

As the substituent of the 'optionally substituted amino group', 'optionally substituted imidoyl group', 'optionally substituted amidino group', 'optionally substituted hydroxyl group' and 'optionally substituted thiol group', as a substituent, for example, lower alkyl groups (e.g., $C_{1-6}$ alkyl group such as methyl, ethyl, propyl, isopropyl, butyl, isobutyl, t-butyl, pentyl, hexyl and the like, etc.), optionally substituted aryl groups (e.g., phenyl, 4-methylphenyl etc.), acyl groups (e.g., $C_{1-6}$ alkanoyl such as formyl, acetyl, propionyl, pivaloyl etc.), arylcarbonyl (e.g., benzoyl etc.), substituted sulfonyl (e.g., alkylsulfonyl such as $C_{1-6}$ alkylsulfonyl (e.g., methylsulfonyl, ethylsulfonyl and the like), $C_{6-14}$ arylsulfonyl (e.g., p-toluenesulfonyl etc.), aminosulfonyl, methylaminosulfonyl, dimethylaminosulfonyl etc.), optionally halogenated $C_{1-6}$ alkoxy-carbonyl (e.g., trifluoromethoxycarbonyl, 2,2,2-trifluoroethoxycarbonyl, trichloromethoxycarbonyl, 2,2,2-trichloroethoxycarbonyl etc.)) and the like can be mentioned.

The 'amino group' of the 'optionally substituted amino group' as a substituent may be substituted by, besides the above-mentioned substituents, optionally substituted imidoyl groups (e.g., $C_{1-6}$ alkylimidoyl, formylimidoyl, amidino etc.) and the like, and in some cases, two substituents together with a nitrogen atom form a cyclic amino group. As the cyclic amino group in such cases, for example, 3- to 8-membered (preferably 5- or 6-membered) cyclic amino and the like, such as 1-azetidinyl; 1-pyrrolidinyl; piperidino (1-piperidinyl); morpholino (4-morpholinyl); 1-piperazinyl; 1-piperazinyl optionally having lower alkyl groups (e.g., $C_{1-6}$ alkyl groups such as methyl, ethyl, propyl, isopropyl, butyl, t-butyl, pentyl, hexyl and the like, etc.), aralkyl groups (e.g., $C_{7-10}$ aralkyl groups such as benzyl, phenethyl and the like, etc.), aryl groups (e.g., $C_{6-10}$ aryl groups such as phenyl, 1-naphthyl, 2-naphthyl and the like, etc.) and the like at the 4-position; and the like can be mentioned.

As the 'optionally substituted carbamoyl group', N-mono-substituted carbamoyl group and N,N-di-substituted carbamoyl group can be mentioned besides the unsubstituted carbamoyl.

The 'N-mono-substituted carbamoyl group' means a carbamoyl group having one substituent on a nitrogen atom, and as the substituent, for example, lower alkyl groups (e.g., $C_{1-6}$ alkyl groups such as methyl, ethyl, propyl, isopropyl, butyl, isobutyl, t-butyl, pentyl, hexyl and the like, etc.), cycloalkyl groups (e.g., $C_{3-6}$ cycloalkyl groups such as cyclopropyl, cyclobutyl, cyclopentyl, cyclohexyl and the like, etc.), aryl groups (e.g., $C_{6-10}$ aryl groups such as phenyl, 1-naphthyl, 2-naphthyl and the like, etc.), aralkyl groups (e.g., $C_{7-10}$ aralkyl groups such as benzyl, phenethyl and the like, preferably phenyl-$C_{1-4}$ alkyl group etc.), heterocyclic groups (e.g., those similar to the 'heterocyclic group' as a substituent of the aforementioned 'optionally substituted hydrocarbon group' denoted by $R^1$, and the like) can be mentioned. The lower alkyl group, cycloalkyl group, aryl group, aralkyl group and heterocyclic group may have a substituent, and as the substituent, for example, hydroxyl group, optionally substituted amino group [said amino group may have, as substituent, 1 or 2 of, for example, lower alkyl groups (e.g., $C_{1-6}$ alkyl groups such as methyl, ethyl, propyl, isopropyl, butyl, isobutyl, t-butyl, pentyl, hexyl and the like, etc.), acyl groups (e.g., $C_{1-6}$ alkanoyl (e.g., formyl, acetyl, propionyl, pivaloyl etc.), arylcarbonyl (e.g., benzoyl etc.), $C_{1-6}$ alkylsulfonyl (e.g., methylsulfonyl, ethylsulfonyl etc.)) and the like], halogen atoms (e.g., fluorine, chlorine, bromine, iodine etc.), nitro group, cyano group, lower alkyl groups (e.g., $C_{1-6}$ alkyl groups such as methyl, ethyl, n-propyl, isopropyl, n-butyl, isobutyl, sec-butyl, tert-butyl, pentyl, hexyl and the like, and the like, with particularly preference given to methyl, ethyl, etc.) optionally substituted by 1 to 5 halogen atoms (e.g., fluorine, chlorine, bromine, iodine etc.), lower alkoxy groups (e.g., $C_{1-6}$ alkoxy groups such as methoxy, ethoxy, n-propoxy, isopropoxy, n-butoxy, isobutoxy, sec-butoxy, tert-butoxy and the like, and the like, with particularly preference given to methoxy, ethoxy and the like) optionally substituted by 1 to 5 halogen atoms (e.g., fluorine, chlorine, bromine, iodine etc.), and the like can be mentioned. These substituents may be the same or different and 1 or 2 or 3 (preferably 1 or 2) thereof preferably substitute.

The 'N,N-di-substituted carbamoyl group' means a carbamoyl group having two substituents on the nitrogen atom, wherein the two substituents on the nitrogen atom may be the same or different. Examples of one of the substituents include those similar to the substituents of the above-mentioned 'N-mono-substituted carbamoyl group', and examples of the other of the substituents include lower alkyl groups (e.g., $C_{1-6}$ alkyl groups such as methyl, ethyl, propyl, isopropyl, butyl, t-butyl, pentyl, hexyl and the like etc.), $C_{3-6}$ cycloalkyl groups (e.g., cyclopropyl, cyclobutyl, cyclopentyl, cyclohexyl etc.), $C_{7-10}$ aralkyl groups (e.g., benzyl, phenethyl and the like, preferably phenyl-$C_{1-4}$ alkyl group etc.) and the like can be mentioned. In addition, two substituents may form a cyclic amino group together with a nitrogen atom, and as the cyclic aminocarbonyl group in such case, for example, 3- to 8-membered (preferably 5- or 6-membered) cyclic amino-carbonyl such as 1-azetidinylcarbonyl; 1-pyrrolidinylcarbonyl; 1-piperidinylcarbonyl; 4-morpholinylcarbonyl; 1-piperazinylcarbonyl; 1-piperazinylcarbonyl having, at the 4-position, lower alkyl groups (e.g., $C_{1-6}$ alkyl groups such as methyl, ethyl, propyl, isopropyl, butyl, t-butyl, pentyl, hexyl and the like, etc.), aralkyl groups (e.g., $C_{7-10}$ aralkyl groups such as benzyl, phenethyl and the like, etc.), aryl groups (e.g., $C_{6-10}$ aryl groups such as phenyl, 1-naphthyl, 2-naphthyl and the like, etc.) and the like; and the like, and the like can be mentioned.

As the substituent of the 'optionally substituted thiocarbamoyl group', those similar to the substituent of the aforementioned 'optionally substituted carbamoyl group' can be mentioned.

As the 'sulfamoyl group optionally having substituents', unsubstituted sulfamoyl as well as N-mono-substituted sulfamoyl group and N,N-di-substituted sulfamoyl group can be mentioned.

The 'N-mono-substituted sulfamoyl group' means a sulfamoyl group having one substituent on the nitrogen atom. As the substituent, those similar to the substituent of the N-mono-substituted carbamoyl group can be mentioned.

The 'N,N-di-substituted sulfamoyl group' means a sulfamoyl group having two substituents on the nitrogen atom. As the substituent, those similar to the substituent of the N,N-di-substituted carbamoyl group can be mentioned.

As the 'optionally esterified carboxyl group', free carboxyl group as well as, for example, lower alkoxycarbonyl group, aryloxycarbonyl group, aralkyloxycarbonyl group and the like can be mentioned.

As the 'lower alkoxycarbonyl group', for example, $C_{1-6}$ alkoxy-carbonyl groups such as methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl and the like and the like can be mentioned. Of these, $C_{1-3}$ alkoxy-carbonyl groups such as methoxycarbonyl, ethoxycarbonyl, propoxycarbonyl and the like, and the like are preferable.

As the 'aryloxycarbonyl group', for example, $C_{6-12}$ aryloxy-carbonyl groups such as phenoxycarbonyl, 1-naphthoxycarbonyl, 2-naphthoxycarbonyl and the like, and the like are preferable.

As the 'aralkyloxycarbonyl group', for example, $C_{7-14}$ aralkyloxy-carbonyl groups such as benzyloxycarbonyl, phenethyloxycarbonyl and the like (preferably $C_{6-10}$ aryl-$C_{1-2}$ alkoxy-carbonyl, etc.), and the like are preferable.

The 'aryloxycarbonyl group' and 'aralkyloxycarbonyl group' may have a substituent, and as the substituent, a similar number of those similar to the substituent of the aryl group and aralkyl group as examples of the substituent of the aforementioned 'N-mono-substituted carbamoyl group' can be used.

As the 'sulfonic acid-derived acyl group' as a substituent, one wherein hydrocarbon group is linked with sulfonyl, and the like can be mentioned, with preference given to acyl such as $C_{1-10}$ alkylsulfonyl, $C_{2-6}$ alkenylsulfonyl, $C_{2-6}$ alkynylsulfonyl, $C_{3-9}$ cycloalkylsulfonyl, $C_{3-9}$ cycloalkenylsulfonyl, $C_{6-14}$ arylsulfonyl, $C_{7-10}$ aralkylsulfonyl and the like can be mentioned. Specific examples of $C_{1-10}$ alkyl include methyl, ethyl, propyl, isopropyl, butyl, isobutyl, t-butyl, pentyl, hexyl, heptyl, octyl and the like. As the $C_{2-6}$ alkenyl, for example, vinyl, allyl, 1-propenyl, isopropenyl, 2-butenyl, 3-butenyl, 2-hexenyl and the like can be mentioned. As the $C_{2-6}$ alkynyl, for example, ethynyl, 2-propynyl, 2-butynyl, 5-hexynyl and the like can be mentioned. As the $C_{3-9}$ cycloalkyl, for example, cyclopropyl, cyclobutyl, cyclopentyl, cyclohexyl, cyclooctyl and the like can be mentioned. As the $C_{3-9}$ cycloalkenyl, for example, 1-cyclopenten-1-yl, 2-cyclopenten-1-yl, 3-cyclopenten-1-yl, 3-cyclohexen-1-yl, 3-cycloocten-1-yl and the like can be mentioned. As the $C_{6-14}$ aryl, phenyl, 1-naphthyl, 2-naphthyl and the like can be mentioned. As the $C_{7-10}$ aralkylsulfonyl, for example, benzyl, phenethyl and the like can be mentioned.

These hydrocarbon groups linked with sulfonyl may have a substituent, and as the substituent, for example, hydroxyl group, optionally substituted amino groups [said amino group may have 1 or 2 substituents from, for example, lower alkyl groups (e.g., $C_{1-6}$ alkyl groups such as methyl, ethyl, propyl, isopropyl, butyl, isobutyl, t-butyl, pentyl, hexyl and the like, etc.), acyl groups (e.g., $C_{1-6}$ alkanoyl (e.g., formyl, acetyl, propionyl, pivaloyl etc.), arylcarbonyl (e.g., benzoyl etc.), $C_{1-6}$ alkylsulfonyl (e.g., methylsulfonyl, ethylsulfonyl etc.)) and the like], halogen atoms (e.g., fluorine, chlorine, bromine, iodine etc.), nitro group, cyano group, lower alkyl group (e.g., $C_{1-6}$ alkyl groups such as methyl, ethyl, n-propyl, isopropyl, n-butyl, isobutyl, sec-butyl, tert-butyl, pentyl, hexyl and the like, and the like, particularly preferably methyl, ethyl and the like) optionally substituted by 1 to 5 halogen atoms (e.g., fluorine, chlorine, bromine, iodine etc.), lower alkoxy group (e.g., $C_{1-6}$ alkoxy group such as methoxy, ethoxy, n-propoxy, isopropoxy, n-butoxy, isobutoxy, sec-butoxy, tert-butoxy and the like, and the like, particularly preferably methoxy, ethoxy and the like) optionally substituted by 1 to 5 halogen atoms (e.g., fluorine, chlorine, bromine, iodine etc.), and the like can be mentioned. These substituents may be the same or different and 1 or 2 or 3 (preferably 1 or 2) thereof preferably substitute.

As the 'carboxylic acid-derived acyl group' as a substituent, one wherein hydrogen atom or a substituent that the aforementioned 'N-mono-substituted carbamoyl group' has on a nitrogen atom is bonded to carbonyl and the like can be mentioned. Preferred are acyl such as $C_{1-6}$ alkanoyl such as formyl, acetyl, trifluoroacetyl, propionyl, butyryl, isobutyryl, pivaloyl and the like, arylcarbonyl such as benzoyl and the like, and the like can be mentioned.

As the alkyl of the 'optionally substituted alkylsulfinyl group' as a substituent, for example, lower alkyl groups such as $C_{1-6}$ alkyl groups (e.g., methyl, ethyl, propyl, isopropyl, butyl, isobutyl, t-butyl, pentyl, hexyl etc.) and the like can be mentioned.

As the aryl of the 'optionally substituted arylsulfinyl group' as a substituent, for example, $C_{6-14}$ aryl groups such as phenyl, naphthyl, anthryl, phenanthryl, acenaphthylenyl and the like and the like can be mentioned.

As the 'substituent' of the 'optionally substituted alkylsulfinyl group' and 'optionally substituted arylsulfinyl group', lower alkoxy groups (e.g., $C_{1-6}$ alkoxy groups such as methoxy, ethoxy, propoxy and the like, etc.), halogen atoms (e.g., fluorine, chlorine, bromine, iodine etc.), lower alkyl groups (e.g., $C_{1-6}$ alkyl groups such as methyl, ethyl, propyl and the like, etc.), amino group, hydroxyl group, cyano group, amidino group and the like can be mentioned. One or two of these optional substituents may be substituted at substitutable positions.

As the 'heterocyclic group optionally having substituents' denoted by $R^4$, those similar to the 'heterocyclic group optionally having substituents' denoted by the following $R^5$ can be mentioned.

As the 'alkoxy group' of the 'alkoxy group optionally having substituents' denoted by $R^4$, for example, $C_{1-6}$ alkoxy such as methoxy, ethoxy, n-propoxy, isopropoxy, n-butoxy, isobutoxy, sec-butoxy, t-butoxy and the like are preferable. As the 'substituent', for example, lower alkyl (e.g., $C_{1-6}$ alkyl such as methyl, ethyl, n-propyl, isopropyl, n-butyl, t-butyl, n-pentyl, n-hexyl and the like), cycloalkyl groups (e.g., $C_{3-6}$ cycloalkyl groups such as cyclopropyl, cyclobutyl, cyclopentyl, cyclohexyl and the like, etc.), aryl groups (e.g., $C_{6-10}$ aryl groups such as phenyl, 1-naphthyl, 2-naphthyl and the like, etc.), aralkyl groups (e.g., $C_{7-10}$ aralkyl groups such as benzyl, phenethyl and the like, preferably phenyl-$C_{1-4}$ alkyl group, etc.), heterocyclic groups (e.g., those similar to 'heterocyclic group' as a substituent of the above-mentioned 'hydrocarbon group' optionally having substituent' denoted by $R^4$, etc.) and the like can be mentioned.

The lower alkyl group, cycloalkyl group, aryl group, aralkyl group and heterocyclic group may have a substituent, and as the substituent, for example, hydroxyl group, optionally substituted amino group [said amino group may have 1 or 2 substituents from, for example, lower alkyl groups (e.g., $C_{1-6}$ alkyl groups such as methyl, ethyl, propyl, isopropyl, butyl, isobutyl, t-butyl, pentyl, hexyl and the like etc.), acyl groups (e.g., $C_{1-6}$ alkanoyl such as formyl, acetyl, propionyl, pivaloyl and the like, arylcarbonyl such as benzoyl and the like, $C_{1-6}$ alkylsulfonyl such as methylsulfonyl, ethylsulfonyl and the like, etc.) and the like], halogen atoms (e.g., fluorine, chlorine, bromine, iodine, etc.), nitro group, cyano group, lower alkyl group optionally substituted by 1 to 5 halogen atoms (e.g., fluorine, chlorine, bromine, iodine, etc.), lower alkoxy group optionally substituted by 1 to 5 halogen atoms (e.g., fluorine, chlorine, bromine, iodine, etc.) and the like can be mentioned. As the lower alkyl group, for example, $C_{1-6}$ alkyl groups such as methyl, ethyl, n-propyl, isopropyl, n-butyl, isobutyl, sec-butyl, t-butyl, pentyl, hexyl and the like, and the like can be mentioned, particularly methyl, ethyl and the like are preferable. As the lower alkoxy group, for example, $C_{1-6}$ alkoxy groups such as methoxy, ethoxy, n-propoxy, isopropoxy, n-butoxy, isobutoxy, sec-butoxy, t-butoxy and the like, and the like can be mentioned, with particular preference given to methoxy, ethoxy and the like. These substituents are the same or different and 1 or 2 or 3 (preferably 1 or 2) thereof are preferably used for substitution.

As the 'aryl group' of the 'aryloxy group optionally having substituents' denoted by $R^4$, for example, $C_{6-14}$ aryl groups such as phenyl, naphthyl, anthryl, phenanthryl, acenaphthylenyl and the like, and the like can be mentioned. As the 'substituent', lower alkoxy groups (e.g., $C_{1-6}$ alkoxy groups such as methoxy, ethoxy, propoxy and the like, etc.), halogen atoms (e.g., fluorine, chlorine, bromine, iodine, etc.), lower alkyl groups (e.g., $C_{1-6}$ alkyl groups such as methyl, ethyl, propyl and the like, etc.), amino group, hydroxyl group, cyano group, amidino group and the like can be mentioned. One or two of these optional substituents may substitute at substitutable positions.

As the 'substituent' of the 'amino group optionally having substituents' denoted by $R^4$, for example, lower alkyl groups (e.g., $C_{1-6}$ alkyl groups such as methyl, ethyl, propyl, isopropyl, butyl, isobutyl, t-butyl, pentyl, hexyl and the like, etc.), acyl groups (e.g., $C_{1-6}$ alkanoyls such as formyl, acetyl, propionyl, pivaloyl, etc., arylcarbonyl (e.g., benzoyl, etc.)), optionally halogenated $C_{1-6}$ alkoxy-carbonyl (e.g., trifluoromethoxycarbonyl, 2,2,2-trifluoroethoxycarbonyl, trichloromethoxycarbonyl, 2,2,2-trichloroethoxycarbonyl, etc.) and the like can be mentioned. The 'amino group' of the 'amino group optionally having substituents' denoted by $R^4$ may be substituted by optionally substituted imidoyl group (e.g., $C_{1-6}$ alkylimidoyl, formylimidoyl, amidino, etc.) and the like. In some cases, two substituents form a cyclic amino group together with nitrogen atom, as the cyclic amino group in such case, for example, 3-to 8-membered (preferably 5- or 6-membered) cyclic amino groups such as 1-azetidinyl, 1-pyrrolidinyl, 1-piperidinyl, 4-morpholinyl, 1-piperazinyl and 1-piperazinyl optionally having, at the 4-position, lower alkyl groups (e.g., $C_{1-6}$ alkyl groups such as methyl, ethyl, propyl, isopropyl, butyl, t-butyl, pentyl, hexyl and the like, etc.), aralkyl groups (e.g., $C_{7-10}$ aralkyl groups such as benzyl, phenethyl and the like, etc.), aryl groups (e.g., $C_{6-10}$ aryl groups such as phenyl, 1-naphthyl, 2-naphthyl and the like, etc.) and the like, and the like, and the like can be mentioned.

As $R^4$, $C_{1-3}$ alkyl, phenyl optionally having substituents, 3-pyridyl, 4-pyridyl and the like are preferable. Particularly, methyl group is preferable.

As the 'cyclic hydrocarbon group' of the 'cyclic hydrocarbon group optionally having substituents' denoted by $R^5$, alicyclic hydrocarbon group, aryl group and the like can be mentioned.

As the alicyclic hydrocarbon group, for example, saturated or unsaturated alicyclic hydrocarbon groups such as cycloalkyl group, cycloalkenyl group, cycloalkanedienyl group and the like can be mentioned. Preferred is cycloalkyl group. As the cycloalkyl group, for example, $C_{3-9}$ cycloalkyl (preferably $C_{3-8}$ cycloalkyl, etc.) such as cyclopropyl, cyclobutyl, cyclopentyl, cyclohexyl, cycloheptyl, cyclooctyl, cyclononyl and the like, and the like, and fused rings such as 1-indanyl, 2-indanyl and the like, can be mentioned. As the cycloalkenyl group, for example, $C_{3-6}$ cycloalkenyl groups such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl and the like, and the like can be mentioned. As the cycloalkanedienyl group, for example, $C_{4-6}$ cycloalkadienyl groups such as 2,4-cyclopentadien-1-yl, 2,4-cyclohexadien-1-yl, 2,5-cyclohexadien-1-yl and the like, and the like can be mentioned.

As the aryl group, for example, monocyclic or condensation polycyclic aromatic hydrocarbon groups can be mentioned, with preference given to $C_{6-14}$ aryl groups such as phenyl, naphthyl, anthryl, phenanthryl, acenaphthylenyl, 4-indanyl, 5-indanyl and the like, and the like. Of these, phenyl, 1-naphthyl, 2-naphthyl and the like are particularly preferable.

As the 'substituent' of the 'cyclic hydrocarbon group optionally having substituents' denoted by $R^5$, those mentioned as the 'substituent' of the aforementioned 'hydrocarbon group optionally having substituents' denoted by $R^4$ can be mentioned. When the cyclic hydrocarbon group is an alicyclic hydrocarbon group, for example, phenyl group, phenyl group optionally substituted by $C_{1-6}$ alkyl such as tolyl group and the like, naphthyl group and the like can be mentioned. When the cyclic hydrocarbon group is an aryl group, for example, halogen atoms (e.g., chlorine atom, fluorine atom, etc.), $C_{1-6}$ alkyl groups (e.g., methyl, ethyl, propyl, isopropyl, butyl, isobutyl, t-butyl, pentyl, hexyl, etc.), $C_{1-6}$ alkoxy groups (e.g., methoxy, ethoxy, n-propoxy, isopropoxy, n-butoxy, etc.), $C_{3-6}$ cycloalkyl groups (e.g., cyclopropyl, cyclobutyl, cyclopentyl, cyclohexyl, etc.), halogenated $C_{1-6}$ alkyl groups (e.g., trifluoromethyl, etc.), halogenated $C_{1-6}$ alkoxy groups (e.g., trifluoromethyloxy, etc.), $C_{1-6}$ alkylthio groups (e.g., methylthio, ethylthio, etc.), $C_{1-6}$ alkylsulfonyl groups (e.g., methylsulfonyl, ethylsulfonyl, etc.), cyano group, nitro group and the like can be mentioned.

As the 'heterocyclic group' of the 'heterocyclic group optionally having substituents' denoted by $R^5$, for example, aromatic heterocyclic group and saturated or unsaturated non-aromatic heterocyclic group (aliphatic heterocyclic group), containing, as a ring-constituting atom (ring atom), at least 1 (preferably 1 to 4, more preferably 1 or 2) of 1 to 3 kinds (preferably 1 or 2 kinds) of hetero atoms, which is selected from oxygen atom, sulfur atom and nitrogen atom, and the like, and the like can be mentioned.

As the aromatic heterocyclic group, aromatic monocyclic heterocyclic groups (e.g., 5- or 6-membered aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like) and aromatic fused heterocycle groups [e.g., 8- to 12-membered aromatic fused heterocycle groups such as benzofuranyl, isobenzofuranyl, benzothienyl, indolyl, isoindolyl, 1H-indazolyl, benzindazolyl, benzoxazolyl, 1,2-benzisoxazolyl, benzothiazolyl, benzopyranyl, 1,2-benzisothiazolyl, benzodioxolyl, benzimidazolyl, 2,1,1-benzoxadiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenathridinyl, phenathrolinyl, indolizinyl, pyrrolo[1,2-b]pyridazinyl, pyrazolo[1,5-a]pyridyl, pyrazolo[3,4-b]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like (preferably a heterocycle wherein the aforementioned 5- or 6-membered aromatic monocyclic heterocyclic group is condensed with a benzene ring or a heterocycle wherein the same or different two heterocycles of the aforementioned 5- or 6-membered aromatic monocyclic heterocyclic group are condensed)] and the like can be mentioned.

As the non-aromatic heterocyclic group, for example, 3-to 8-membered (preferably 5- or 6-membered) saturated or unsaturated (preferably saturated) non-aromatic heterocyclic groups (aliphatic heterocyclic groups) such as oxiranyl, azetidinyl, oxetanyl, thietanyl, pyrrolidinyl, tetrahydrofuryl, thiolanyl, piperidinyl, tetrahydropyranyl, morpholinyl, thiomorpholinyl, piperazinyl and the like, and the like can be mentioned.

As the 'substituent' of the 'heterocyclic group optionally having substituents' denoted by $R^5$, those mentioned as the 'substituent' of the aforementioned 'hydrocarbon group optionally having substituents' denoted by $R^4$ can be mentioned.

As the $R^5$, phenyl groups optionally having substituents are preferable. Of these, a phenyl group having 1 or 2 substituents selected from the group consisting of halogen atom and methyl group is particularly preferable.

As the $G^1$, carbonyl (CO) is preferable.

The compound represented by the formula (IX) can form a salt, and as such salt, those similar to the salts of the compound represented by the formula (I) can be mentioned. In the following, a compound represented by the formula (IX) and a salt thereof are simply referred to as Compound (IX).

The reaction between Compound (VIII) and Compound (IX) can be carried out according to the method described in ORGANIC FUNCTIONAL GROUP PREPARATIONS, the second edition, ACADEMIC PRESS, INC.

This reaction is generally carried out in a solvent inert to the reaction. As such solvent, alcohol solvent, ether solvent, halogen solvent, aromatic solvent, acetonitrile, N,N-dimethylformamide (DMF), acetone, methyl ethyl ketone, dimethyl sulfoxide (DMSO) and the like can be used alone or in a mixture. Of these, acetonitrile, dimethylformamide, acetone, ethanol and the like are preferable.

Compound (VIII) is generally used in an amount of 0.8 mole to 1.5 moles, preferably 1 mole to 1.3 moles, per 1 mole of Compound (IX). The reaction temperature is generally from room temperature to 100° C., preferably 30° C. to 90° C., and the reaction time is generally 0.5 hr. to 1 day.

In this reaction, 1 to 5 equivalents of a base is generally added relative to Compound (IX), but it is not necessarily essential. As such base, 1) strong bases such as hydrides of alkali metal or alkaline earth metal (e.g., lithium hydride, sodium hydride, potassium hydride, calcium hydride, etc.), amides of alkali metal or alkaline earth metal (e.g., lithium amide, sodium amide, lithium diisopropylamide, lithium dicyclohexylamide, lithium hexamethyl disilazide, sodium hexamethyl disilazide, potassium hexamethyl disilazide, etc.), lower alkoxides of alkali metal or alkaline earth metal (e.g., sodium methoxide, sodium ethoxide, potassium t-butoxide, etc.) and the like, 2) inorganic bases such as hydroxides of alkali metal or alkaline earth metal (e.g., sodium hydroxide, potassium hydroxide, lithium hydroxide, barium hydroxide, etc.), carbonates of alkali metal or alkaline earth metal (e.g., sodium carbonate, potassium carbonate, cesium carbonate, etc.), hydrogencarbontes of alkali metal or alkaline earth metal (e.g., sodium hydrogencarbonate, potassium hydrogencarbonate, etc.) and the like, 3) organic bases such as amines of triethylamine, diisopropylethylamine, N-methylmorpholine, dimethylaminopyridine, DBU (1,8-diazabicyclo[5.4.0]-7-undecene), DBN (1,5-diazabicyclo[4.3.0] non-5-ene) and the like, basic heterocyclic compounds such as pyridine imidazole, 2,6-lutidine and the like, and the like can be mentioned.

To promote the reaction, for example, alkali metal iodides such as potassium iodide, sodium iodide and the like are desirably co-used. Of these, co-use of potassium iodide is particularly preferable. The alkali metal iodide is generally used in an amount of 0.1 mole to 5 moles, preferably 0.5 mole to 3 moles, per 1 mole of Compound (IX).

As the salt of the compound of the formula (X), acid addition salts such as inorganic acid salts (e.g., hydrochloride, sulfate, hydrobromide, phosphate, etc.), organic acid salts (e.g., acetate, trifluoroacetate, succinate, maleate, fumarate, propionate, citrate, tartrate, lactate, oxalate, methanesulfonate, p-toluenesulfonate, etc.) and the like, salts with bases (e.g., alkali metal salts such as potassium salt, sodium salt, lithium salt and the like, alkaline earth metal salts such as calcium salt, magnesium salt and the like, salts with organic bases such as ammonium salt, trimethylamine salt, triethylamine salt, t-butyldimethylamine salt, dibenzylmethylamine salt, benzyldimethylamine salt, N,N-dimethylaniline salt, pyridine salt, quinoline salt and the like) may be formed.

In the following, a compound represented by the formula (X) and a salt thereof are simply referred to as Compound (X).

The Compound (IX) used as a starting material in this reaction can be synthesized by using a compound represented by the formula:

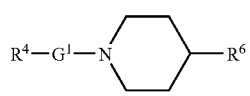

(XIII)

wherein $R^6$ is a carboxyl group, a sulfonic acid group or a salt thereof or a reactive derivative thereof, and other symbols are as defined above, or a salt thereof, as a starting material according to a conventionally known method. In some cases, the compound represented by the formula (XIII) can form a salt, and such salt, those similar to the salts of the compound represented by the formula (I), as well as acid addition salts such as inorganic acid salts (e.g., hydrochloride, sulfate, hydrobromide, phosphate, etc.), organic acid salts (e.g., acetate, trifluoroacetate, succinate, maleate, fumarate, propionate, citrate, tartrate, lactate, oxalate, methanesulfonate, p-toluenesulfonate, etc.) and the like can be mentioned. In the following, a compound represented by the formula (XIII) and a salt thereof are simply referred to as Compound (XIII). In Compound (XIII), a compound, wherein $R^6$ is a carboxyl group, or a salt thereof corresponds to a compound represented by the aforementioned the formula (XII) or a salt thereof. In the following, a compound represented by the formula (XII) and a salt thereof are simply referred to as Compound (XII). Of the Compound (XIII), Compound (XII) is preferable.

As the reactive derivative of carboxy group denoted by $R^6$, for example, a reactive derivative such as acid halide, acid azide, acid anhydride, mixed acid anhydride, active amide, active ester, active thio ester, isocyanate and the like is subjected to acylation reaction. As the acid halide, for example, acid chloride, acid bromide and the like can be mentioned.

As the mixed acid anhydride, for example, mono $C_{1-6}$ alkyl carbonate mixed acid anhydride (e.g., mixed acid anhydride of free acid and monomethyl carbonate, monoethyl carbonate, monoisopropyl carbonate, monoisobutyl carbonate, mono-t-butyl carbonate, monobenzyl carbonate, mono (p-nitrobenzyl) carbonate, monoallyl carbonate and the like), $C_{1-6}$ aliphatic carboxylic mixed acid anhydride (e.g., mixed acid anhydride of free acid and acetic acid, trichloroacetic acid, cyanoacetic acid, propionic acid, butyric acid, isobutyric acid, valeric acid, isovaleric acid, pivalic acid, trifluoroacetic acid, trichloroacetic acid, acetoacetic acid and the like), $C_{7-12}$ aromatic carboxylic mixed acid anhydride (e.g., mixed acid anhydride of free acid and benzoic acid, p-toluic acid, p-chlorobenzoic acid and the like), organic sulfonic mixed acid anhydride (e.g., mixed acid anhydride of free acid and methanesulfonic acid, ethanesulfonic acid, benzenesulfonic acid, p-toluenesulfonic acid and the like) and the like can be mentioned.

As the active amide, for example, amide with nitrogen-containing heterocyclic compound [e.g., acid amide of free acid and pyrazole, imidazole, benzotriazole and the like, wherein these nitrogen-containing heterocyclic compounds are optionally substituted by $C_{1-6}$ alkyl groups (e.g., methyl, ethyl, etc.), $C_{1-6}$ alkoxy groups (e.g., methoxy, ethoxy, etc.), halogen atoms (e.g., fluorine, chlorine, bromine, etc.), oxo groups, thioxo group, $C_{1-6}$ alkylthio groups (e.g., methylthio, ethylthio, etc.) and the like] and the like can be mentioned.

As the active ester, any that can be used for this object in the field of β-lactam and peptide syntheses can be used. For example, organic phosphoric acid ester (e.g., diethoxyphosphoric acid ester, diphenoxyphosphoric acid ester, etc.), as well as p-nitrophenyl ester, 2,4-dinitrophenyl ester, cyanomethyl ester, pentachlorophenyl ester, N-hydroxysuccinimide ester, N-hydroxyphthalimide ester, 1-hydroxybenzotriazole ester, 6-chloro-1-hydroxybenzotriazole ester, 1-hydroxy-1H-2-pyridone ester and the like can be mentioned.

As the active thio ester, for example, ester with aromatic heterocycle thiol compound [e.g., 2-pyridylthiol ester, 2-benzothiazolylthiol ester and the like, wherein these heterocycles are optionally substituted by $C_{1-6}$ alkyl groups (e.g., methyl, ethyl, etc.), $C_{1-6}$ alkoxy groups (e.g., methoxy, ethoxy, etc.), halogen atoms (e.g., fluorine, chlorine, bromine, etc.), $C_{1-6}$ alkylthio groups (e.g., methylthio, ethylthio, etc.) and the like] can be mentioned.

As the 'reactive derivative of sulfonic acid group' denoted by $R^6$, for example, sulfonyl halides (e.g., sulfonyl chloride, sulfonyl bromide, etc.), sulfonylazide, acid anhydrides thereof and the like can be mentioned.

The Compound (IX) can be produced, for example, by reacting Compound (XII) with a compound represented by the formula:

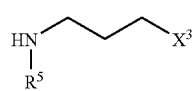

(XI)

or a salt thereof. The compound represented by the formula (XI) can form a salt, and as such salt, those similar to the salt of the compound represented by the formula (I) can be mentioned. In the following, a compound represented by the formula (XI) and a salt thereof are simply referred to as Compound (XI).

The reaction between Compound (XII) and Compound (XI) is generally carried out via a reactive derivative of carboxyl group, and the reactive derivative may or may not be isolated. As the reactive derivative of carboxyl group, those mentioned above can be used. Generally, acid chloride is used, which is comparatively easily prepared and advantageous in cost.

The solvent to be used for this reaction may be any as long as it does not inhibit the reaction. For example, hydrocarbons (e.g., n-hexane, n-heptane, benzene, toluene, xylene etc.), halogenated hydrocarbons (e.g., dichloromethane etc.), ethers (e.g., diethyl ether, diisopropyl ether, ethylene glycol dimethyl ether, tetrahydrofuran, dioxane etc.), amides (e.g., N,N-dimethylformamide, N,N-dimethylacetamide, N-methylpyrrolidone etc.), esters (e.g., ethyl acetate, methyl acetate etc.), nitriles (e.g., acetonitrile etc.), sulfoxides (e.g., dimethyl sulfoxide etc.), ketones (e.g., acetone, 2-butanone, 4-methyl-2-pentanone, cyclohexanone, etc.) and the like can be mentioned. Of these, hydrocarbons (e.g., n-hexane, n-heptane, benzene, toluene, xylene etc.), ethers (e.g., diethyl ether, diisopropyl ether, ethylene glycol dimethyl ether, tetrahydrofuran, dioxane etc.), amides (e.g., N,N-dimethylformamide, N,N-dimethylacetamide, N-methylpyrrolidone etc.), esters (e.g., ethyl acetate, methyl acetate etc.), nitriles (e.g., acetonitrile etc.) and ketones (e.g., acetone, 2-butanone, 4-methyl-2-pentanone, cyclohexanone etc.) are preferable. These solvents may be used alone or in a mixture of two or more kinds.

The Compound (XII) is generally used in an amount of 1 mole to 3 moles, preferably 1 mole to 2 moles, per 1 mole of Compound (XI). The reaction between Compound (XII) and Compound (XI) is carried out generally at −20° C. to 100° C., preferably 0° C. to 30° C., for 30 min. to 6 hrs., preferably 1 hr. to 3 hrs.

For conversion of —COOH group to —COCl group, thionyl chloride and the like are preferably and used generally in an amount of 1 mole to 30 moles, preferably 1 mole to 10 moles, per 1 mole of Compound (XII). For isolation of acid chloride, it may be used in around 30 moles also as a solvent, and when the reaction with Compound (XI) is continued without isolation of an acid chloride, it is more preferably used in 1 mole to 2 moles. This conversion is performed generally at −20° C. to 100° C., preferably 0° C. to 60° C., for 5 min. to 6 hrs., preferably 10 min. to 3 hrs.

The Compound (XII) can be obtained easily from, for example, commercially available isonipecotic acid derivatives by alkylation reaction, acylation reaction, sulfonylation and the like known per se, and some may be available as commercial products. The Compound (XI) can be obtained from commercially available or known aniline derivative by a method known per se, such as N-alkylation and the like.

The compound or a salt thereof obtained by the above-mentioned method can be isolated or purified by, for example, a means such as solvent extraction, concentration under reduced pressure, crystallization, recrystallization, distillation, chromatography and the like.

The compound or a salt thereof obtained by the above-mentioned method can be used in the next step as a reaction mixture or without thorough purification.

In the invention of the above-mentioned (3)–(7), when Compound (IV) is reacted with Compound (V), Compound (I) is produced in the reaction mixture. The Compound (I) can be led to Compound (III) without isolation but by reaction with Compound (II).

The Compound (X) can be used together with other prophylactic or therapeutic agents of HIV infectious diseases (particularly, prophylactic or therapeutic agent of AIDS). In this case, these drugs are separately or simultaneously, admixed with pharmacologically acceptable carriers, excipients, binders, diluents and the like for forming a preparation and can be administered orally or parenterally as a pharmaceutical composition for the prophylaxis or treatment of HIV infectious diseases. When drugs are independently prepared, the separately prepared agents can be administered upon mixing by the use of diluent and the like when in use, but each preparation separately prepared may be administered simultaneously or in a staggered manner to a single subject. A kit product for administration upon mixing separately prepared drugs using a diluent and the like when in use (e.g., injection kit containing ampoules each containing powder drug, a diluent to dissolve two or more drugs in admixture when in use and the like, etc.), a kit product for simultaneous or staggered separate administration of separately prepared drugs to a single subject (e.g., a tablet kit for independent, simultaneous or staggered administration of two or more tablets containing each drug placed in the same or different bag(s) having, where necessary, a column to indicate the time of administration of the drug, etc.) and the like may be prepared.

Specific examples of the prophylactic or therapeutic agent of HIV infectious diseases to be used together with Compound (X) include nucleic acid reverse transcription enzyme inhibitors such as zidovudine, didanosine, zalcitabine, lamivudine, stavudine, abacavir, adefovir, adefovir dipivoxil, fozivudine tidoxil and the like; non-nucleic acid reverse transcription enzyme inhibitors such as nevirapine, delavirdine, efavirenz, loviride, immunocal, oltipraz and the like, including pharmaceutical agents having an anti-oxidization action such as immunocal, oltipraz and the like; protease inhibitors such as saquinavir, ritonavir, indinavir, nelfinavir, amprenavir, palinavir, lasinavir and the like; and the like.

As the nucleic acid reverse transcription enzyme inhibitors, zidovudine, didanosine, zalcitabine, lamivudine, stavudine, abacavir and the like are preferable, and as the non-nucleic acid reverse transcription enzyme inhibitors, nevirapine, delavirdine, efavirenz and the like are preferable. As the protease inhibitors, saquinavir, ritonavir, indinavir, nelfinavir, amprenavir and the like are preferable.

The Compound (X) can be also used in combination with the above-mentioned protease inhibitors, nucleic acid reverse transcription enzyme inhibitors and the like, as well as, for example, CXCR4 antagonists (e.g., AMD-8664, etc.), which are T cell oriented HIV-1 second receptors, CD4 antagonist, entry inhibitors (e.g., T-20, FP-21399, etc.) that inhibit invasion of viruses into host cells by acting on the surface antigens of HIV-1, integrase inhibitors that inhibit incorporation of virus DNA into host chromosomes, Tat inhibitors that inhibit transcription of virus DNA to mRNA by acting on Tat, which is an HIV-1 transcription factor, and HIV-1 vaccines.

The Compound (X) that can be obtained from Compound (VIII) by the method of the present invention has a CCR antagonistic action, particularly potent CCR5 antagonistic action, and is low toxic. Therefore, it can be used as a prophylactic or therapeutic agent such as a prophylactic or therapeutic agent of various HIV infectious diseases in humans, such as AIDS, and a suppressant of the disease state of AIDS, a prophylactic or therapeutic agent of multiple sclerosis, a prophylactic or therapeutic agent of graft versus host reaction, a prophylactic or therapeutic agent of chronic rheumatism and the like. Compound (X) can be administered orally or parenterally as a pharmaceutical preparation made from starting materials conventionally used for pharmaceutical preparations such as excipient, diluent, extender and the like.

The daily dose of Compound (X) varies depending on the conditions and body weight of patients and the administration method. In the case of oral administration, the dose of the active ingredient [Compound (X)] is ca. 5 to 1000 mg, preferably ca. 10–600 mg, more preferably ca. 10–300 mg, particularly preferably ca. 15–150 mg, for an adult (body weight 50 kg), which is administered once or in 2 or 3 portions a day.

When Compound (X) and a reverse transcription enzyme inhibitor and/or a protease inhibitor are used in combination, the dose of the reverse transcription enzyme inhibitor or protease inhibitor is appropriately determined from the range of, for example, not less than about 1/200 to 1/2 and not more than about 2 to 3 times the typical dose. In addition, when 2 or more kinds of pharmaceutical agents are used in combination, and one pharmaceutical agent affects the metabolism of the other pharmaceutical agent(s), the dose of each pharmaceutical agent is appropriately adjusted, but in general, the dose of single administration of each pharmaceutical agent is used.

EXAMPLES

The present invention is explained in more detail in the following by referring to Reference Examples and Examples. The present invention is not limited in any way by these examples.

In the present specification, by the 'room temperature' is meant a range of 20–30° C. and approximately 25° C., and by the 'overnight' is meant about 15 hrs.

Example 1

Production of 4-(chloromethyl)benzamide

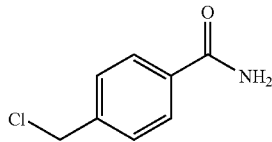

To a mixture of 28% aqueous ammonia (19.3 g, 317 mmol, 4.0 eq) and toluene (30 mL) was dropwise added a 4-chloromethylbenzoyl chloride. (15.0 g, 79.3 mmol)/toluene (30 mL) solution under ice-cooling. The mixture was stirred at room temperature for 1 hr. and under ice-cooling for 1 hr. The crystals were collected by filtration, washed with water (9 mL) and toluene (9 mL), and dried in vacuo at 40° C. to give the title compound (13.36 g, yield 99.3%) as white crystals.

$^1$H-NMR (300 MHz, CDCl$_3$) δ: 1.37 (3H, t, J=7.1 Hz), 2.05 (2H, quint, J=6.7 Hz), 2.54 (2H, t, J=6.7 Hz), 2.60 (3H, s), 3.19 (2H, t, J=6.7 Hz), 4.33 (2H, q, J=7.1 Hz)

Example 2

Diethyl 4-carbamoylbenzylphosphonate

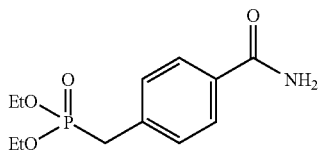

The compound (44.83 g, 0.264 mol) obtained in Example 1, triethyl phosphite (53.21 g, 0.320 mol), potassium iodide (39.4 g, 0.237 mol) and acetonitrile (224 mL) were charged and stirred under reflux for 4 hrs. The reaction mixture was allowed to return to room temperature, and water (336 mL) was added. The mixture was concentrated under reduced pressure, and the residue (315 g) was stirred at room temperature for 1 hr. and under ice-cooling for 1 hr. The crystals were collected by filtration, washed with cold water (20 mL) and dried in vacuo at 40° C. for 7 hrs. to give the title compound (66.79 g, yield 93.2%) as slightly yellow crystals.

$^1$H-NMR (300 MHz, CDCl$_3$)δ: 1.27 (6H, t, J=7.1 Hz), 3.22 (2H, t, J=11.0 Hz), 3.99–4.10 (4H, m), 7.37–7.85 (4H, m).

Example 3

Production of 4-(1-benzylpiperidin-4-ylidenemethyl)benzamide

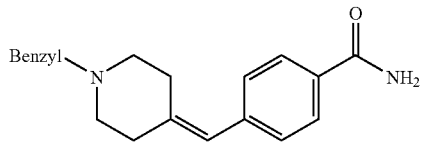

The compound (25.0 g, 0.147 mol) obtained in Example 1, triethyl phosphite (29.4 g, 0.177 mol), potassium iodide (22.0 g, 0.133 mol) and acetonitrile (125 mL) were charged and stirred under reflux for 3 hrs. The reaction mixture was allowed to return to room temperature, and concentrated under reduced pressure. To the residue were added N,N-dimethylformamide (100 mL) and 1-benzyl-4-piperidone (30.6 g, 0.162 mol), and the mixture was stirred under ice-cooling. Potassium t-butoxide (23.1 g, 0.206 mol) was added in 3 portions at 15 min. intervals. The reaction mixture was stirred at room temperature for 45 min. Water (400 mL) was dropwise added under ice-cooling, and the mixture was stirred for 30 min. Crystals were collected by filtration, washed with cold water (180 mL) and dried in vacuo at 40° C. to give the title compound (38.7 g, yield 85.2%) as pale-yellow powdery crystals.

$^1$H-NMR (300 MHz, CDCl$_3$)δ: 2.40–2.57 (8H, m), 3.54 (2H, s), 6.04 (2H, br.s, NH$_2$), 6.29 (1H, s), 7.25–7.77 (9H, m).

Example 4

Production of 4-(4-piperidylmethyl)benzamide

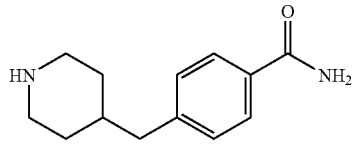

The compound (4267.9 g, 13.929 mol) obtained in Example 3, 10% palladium carbon (889.4 g, ca. 50% water-containing product) and methanol (38.4 L) were charged, and a hydrogenation reaction was conducted at normal pressure at 50° C. for 5 hrs. After the reaction, the reaction mixture was separated by filtration without cooling to remove the insoluble material and washed with methanol (3 L). The reaction mixture was concentrated under reduced pressure to about 10 L, and ethyl acetate (15 L) was added, followed by concentration again under reduced pressure to about 10 L, which step was conducted twice. The residue (ca. 10 L) was stirred under reflux for 2 hrs., and cooled to room temperature. The crystals were collected by filtration, washed with ethyl acetate (2 L) and dried in vacuo at 40° C. to give the title compound (2619.2 g, yield 86.1%) as white crystals.

$^1$H-NMR (300 MHz, CDCl$_3$)δ: 1.14–1.19 (2H, m), 1.59–1.63 (3H, m), 2.49–2.59 (4H, m), 3.03–3.07 (2H, m), 7.21–7.75 (4H, m).

Reference Example 1

Production of 4-(1-benzylpiperidin-4-ylidenemethyl)benzamide

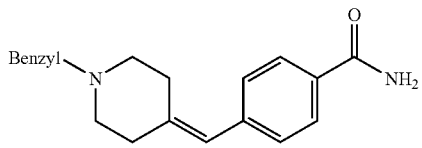

4-Cyanobenzyl bromide (4.90 g, 25.0 mmol), triethyl phosphite (4.77 mL, 27.5 mmol) and toluene (4.9 mL) were charged, and the mixture was stirred with heating under reflux for 3 hrs., while distilling away the solvent at normal pressure. The mixture was allowed to return to room temperature, and concentrated under reduced pressure to give a colorless transparent oil which solidified by standing. N-benzylpiperidone (4.73 g, 25.0 mmol), ethanol (35 mL), water (451 mg, 25.0 mmol) and potassium hydroxide (pellet, 7.01 g, 125 mmol) were added successively, and the mixture was stirred at room temperature for 30 min. to give a yellow solution. The solution was stirred at 65–70° C. for 2 hrs. and cooled to 60° C. to allow precipitation of crystals to give a yellow suspension. Iced water (200 mL) was added, and the mixture was stirred at 0–5° C. After dissolution once, a yellow suspension was formed. The suspension was stirred at 0–5° C. for 30 min. and the crystals were collected by filtration and dried in vacuo at 40° C. to give the title compound (3.30 g, yield 43.0%) as white crystals.

$^1$H-NMR (300 MHz, CDCl$_3$)δ: 2.40–2.57 (8H, m), 3.54 (2H, s), 6.04 (2H, br.s, NH$_2$), 6.29 (1H, s), 7.25–7.77 (9H, m).

Example 5

Production of 4-(4-piperidylmethyl)benzamide

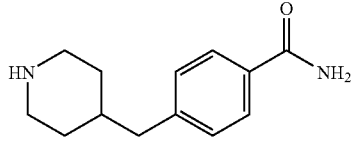

The compound (0.919 g, 3.00 mmol) obtained in Reference Example 1, 10% palladium carbon (0.192 g, ca. 50% water-containing product) and methanol (9.2 mL) were charged, and the mixture was stirred vigorously under hydrogen atmosphere at 50° C. for 3 hrs. Insoluble materials were filtered off, and the residue was washed with methanol (2.0 mL) and concentrated under reduced pressure to give the title compound (0.642 g, yield 98%) as a white dry solid.

$^1$H-NMR (300 MHz, CDCl$_3$)δ: 1.14–1.19 (2H, m), 1.59–1.63 (3H, m), 2.49–2.59 (4H, m), 3.03–3.07 (2H, m), 6.10 (2H, br.s, NH$_2$), 7.21–7.75 (4H, m).

Reference Example 2

Production of 4-(4-piperidylidenemethyl)benzamide

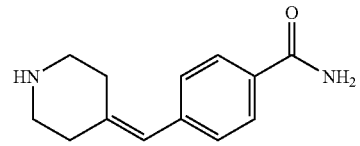

4-Cyanobenzyl bromide (49.0 g, 250 mmol), triethyl phosphite (45.7 g, 275 mmol) and toluene (49 mL) were charged, and the mixture was stirred and heated under reflux for 3 hrs., while distilling away the solvent at normal pressure. Then, the mixture was allowed to return to room temperature and concentrated under reduced pressure to give a colorless transparent oil. 4-Piperidone hydrochloride monohydrate (46.1 g, 300 mmol), ethanol (350 mL) and potassium hydroxide (pellet, 70.1 g, 1250 mmol) were added successively, and the mixture was stirred at room temperature for 30 min. and at 65–70° C. for 4 hrs. to give a pale-yellow suspension. Water (0.5 L) was added to the suspension at 20–25° C., and the mixture was extracted with ethyl acetate (2.0 L) and ethyl acetate-ethanol (17:3, 2.0 L). The obtained organic layers were combined, washed with saturated brine (1.0 L) and concentrated under reduced pressure. To the resulting residue was added ethyl acetate (150 mL), and the mixture was stirred at 0–5° C. for 30 min. The crystals were collected by filtration and dried to give a pale-yellow solid. 2-Propanol (140 mL) was added thereto, and the mixture was stirred at room temperature for 30 min. and further at 0–5° C. for 30 min. The crystals were collected by filtration and dried to give the title compound (17.3 g, yield 41.4%) as pale-yellow crystals.

$^1$H-NMR (300 MHz, CDCl$_3$)δ: 2.32–2.48 (4H, m), 2.83–2.99 (4H, m), 6.00 (2H, br.s, NH$_2$), 6.29 (1H, s), 7.23–7.78 (4H, m).

Example 6

Production of 4-(4-piperidylmethyl)benzamide

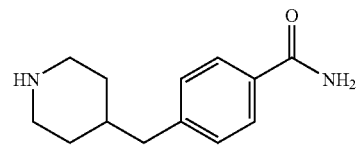

The compound (1.93 g, 8.92 mmol) obtained in Reference Example 2, 10% palladium carbon (50% wet, 569 mg) and tetrahydrofuran (39 mL) were charged, and the mixture was vigorously stirred under a hydrogen atmosphere at 35–40° C. for 1 hr. Insoluble materials were filtered off while hot, and the resulting filtrate was washed with tetrahydrofuran (39 mL), concentrated under reduced pressure to give the title compound (1.93 g, yield 98.7%) as white crystals.

$^1$H-NMR (300 MHz, CDCl$_3$)δ: 1.14–1.19 (2H, m), 1.59–1.63 (3H, m), 2.49–2.59 (4H, m), 3.03–3.07 (2H, m), 6.10 (2H, br.s, NH$_2$), 7.21–7.75 (4H, m).

Reference Example 3

Ethyl 1-mesyl-4-piperidinecarboxylate

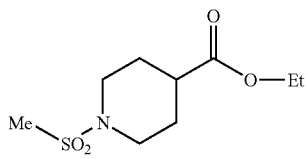

Ethyl isonipecotinate (1.0 g, 6.36 mmol), acetone (5 mL) and triethylamine (0.97 mL, 6.99 mmol) were charged and stirred under ice-cooling. Methanesulfonyl chloride (0.54 mL, 7.02 mmol) was dropwise added, and the mixture was stirred at room temperature for 2 hrs. Water (10 mL) was added dropwise, and the mixture was stirred at room temperature for 30 min. and under ice-cooling for 1 hr. The crystals were collected by filtration, washed with ice-cooling acetone-water (1:3) (2 mL) and water (4 mL), and dried in vacuo at 40° C. for 9 hrs. to give the title compound (1.31 g, yield 87.3%) as white crystals.

$^1$H-NMR (300 MHz, CDCl$_3$)δ: 1.24 (3H, t, J=7.1 Hz), 1.78–1.87 (2H, m), 1.97–2.02 (2H, m), 2.38–2.41 (1H, m), 2.76 (3H, s), 2.79–2.88 (2H, m), 3.61–3.67 (2H, m), 4.23 (2H, q, J=7.1 Hz).

Reference Example 4

1-Mesyl-4-piperidinecarboxylic acid

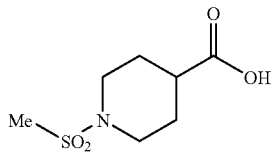

The compound (132.4 g, 563 mmol) obtained in Reference Example 3 and sodium hydroxide (28.4 g, 710 mmol)/water (348 mL) solution were charged, and the mixture was stirred at room temperature for 3 hrs. The reaction mixture was ice-cooled and conc. hydrochloric acid (65 mL, 780 mmol) was dropwise added. The mixture was stirred under ice-cooling for 1 hr. The crystals were collected by filtration, washed with water (100 mL) and dried in vacuo at 40° C. for 9 hrs. to give the title compound (112.7 g, yield 96.6%) as white crystals.

$^1$H-NMR (300 MHz, DMSO)δ: 1.49–1.60 (2H, m), 1.86–1.92 (2H, m), 2.2–2.4 (1H, m), 2.72–2.80 (2H, m), 2.82 (3H, s), 3.42–3.48 (2H, m).

Reference Example 5

1-Mesyl-4-piperidinecarbonyl chloride

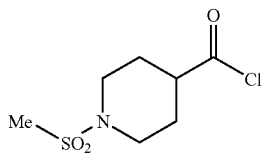

The compound (20.0 g, 96.5 mmol) obtained in Reference Example 4 and thionyl chloride (46.2 g, 388 mmol) were charged, and the mixture was gradually heated to 50° C. over 1.5 hrs and stirred at 50° C. for 2 hrs. The mixture was allowed to return to room temperature, and diisopropyl ether (84 mL) was added dropwise. The reaction mixture was stirred at room temperature for 1 hr. and under ice-cooling for 1 hr. The crystals were collected by filtration, washed with diisopropyl ether (30 mL) and dried in vacuo at room temperature for 7 hrs. to give the title compound (20.8 g, yield 95.5%) as white crystals.

$^1$H-NMR (300 MHz, CDCl$_3$)δ: 1.88–1.96 (2H, m), 2.15–2.21 (2H, m), 2.78 (3H, s), 2.85–2.94 (3H, m), 3.64–3.69 (2H, m).

Reference Example 6

3,4-Dichloro-N-formylaniline

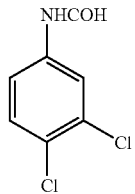

3,4-Dichloroaniline (1000.0 g, 6.172 mol) and formic acid (585 g, 12.7 mol) were charged, and the mixture was stirred at 90° C. for 1 hr. Water (1.5 L) was dropwise added with heating, and then the mixture was gradually cooled to allow precipitation of the crystals. The mixture was stirred at room temperature for 30 min., and the crystals were collected by filtration. The crystals were washed with water (1.2 L) and dried in vacuo at 40° C. for 8 hrs. to give the title compound (1160.8 g, yield 99.0%) as pale-brown crystals.

$^1$H-NMR (300 MHz, DMSO)δ: 7.18–7.97 (3H, m), 8.32–8.85 (1H, m), 10.46 (1H, br.s, NH).

Reference Example 7

3,4-Dichloro-N-(3-chloropropyl)aniline hydrochloride

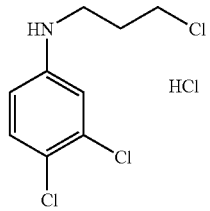

The compound (1160 g, 6.104 mol) obtained in Reference Example 6, acetone (5.8 L), potassium carbonate (2.53 kg, 18.31 mol) and 1-bromo-3-chloropropane (1.81 L, 18.31 mol) were charged, and the mixture was stirred under reflux for 14 hrs. Water (8.7 L) and ethyl acetate (2.9 L) were added, and the mixture was partitioned. To the aqueous layer was added ethyl acetate (2.9 L) for extraction. The obtained organic layers were combined and washed with water (5.8 L) and saturated brine (5.8 L). The mixture was concentrated under reduced pressure to give a brown oily substance (1743.8 g). 2-Propanol (5.8 L) was added to this oily substance (1743.8 g), and conc. hydrochloric acid (1089 mL, 12.2 mol) was dropwise added over 30 min. at room temperature. The mixture was stirred at 60° C. for 1 hr. By ice-cooling, the crystals were precipitated, and the mixture was stirred under ice-cooling for 1.5 hrs. The crystals were collected by filtration, washed with diisopropyl ether (580 ml) and dried in vacuo at 40° C. for 9 hrs. to give the title compound (1509.1 g, yield 89.9%) as yellowish brown crystals.

$^1$H-NMR (300 MHz, DMSO)δ: 1.91–2.00 (2H, m), 3.12 (2H, t, J=6.8 Hz), 3.69 (2H, t, J=6.8 Hz), 6.69–7.32 (3H, m).

Reference Example 8

N-(3-Chloropropyl)-N-(3,4-dichlorophenyl)-1-mesyl-4-piperidine carboxamide

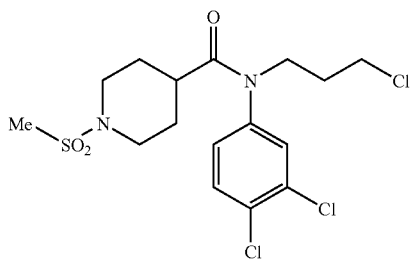

The compound (900.0 g, 3.273 mol) obtained in Reference Example 7 and 1-methyl-2-piperidone (4.5 L) were charged, and the mixture was stirred at room temperature for dissolution. The compound (369 g, 1.635 mol×3) obtained in Reference Example 5 was added under water-cooling at 22–27° C. at 30 min. intervals. After the addition, the mixture was stirred at room temperature for 1.5 hrs. Water (13.5 L) was dropwise added under ice-cooling, and the mixture was stirred at room temperature for 1.5 hrs. The crystals were collected by filtration, washed with water (9 L) and dried in vacuo at 50° C. for 26 hrs. to give the title compound (1372.7 g, yield 98.1%) as white crystals.

$^1$H-NMR (300 MHz, CDCl$_3$)δ: 1.64–1.71 (2H, m), 1.80–2.02 (4H, m), 2.15–2.28 (1H, m), 2.54 (2H, t, J=10.9 Hz), 2.70 (3H, s), 3.51 (2H, t, J=6.5 Hz), 3.65–3.77 (4H, m), 7.00–7.52 (3H, m).

Reference Example 9

N-[3-[4-(4-Carbamoylbenzyl)-1-piperidyl]propyl]-N-(3,4-dichlorophenyl)-1-mesyl-4-piperidine carboxamide

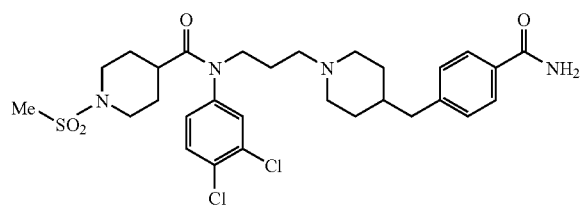

The compound (1350.0 g, 3.156 mol) obtained in Reference Example 8, potassium iodide (529.1 g, 3.187 mol), anhydrous potassium carbonate (1744.7 g, 12.624 mol), compound (757.8 g, 3.471 mol) obtained in Example 4, N,N-dimethylformamide (6.75 L) and acetonitrile (6.75 L) were charged, and the mixture was stirred at 80–85° C. for 2.5 hrs. The mixture was allowed to return to room temperature, and water (27 L) was dropwise added. The mixture was stirred at room temperature for 30 min. and then under ice-cooling for 1 hr. The crystals were collected by filtration, and washed with water (13.5 L). After drying in vacuo at 50° C., acetonitrile (17.2 L) was charged, and the mixture was stirred under reflux for 2 hrs. The mixture was allowed to return to room temperature and stirred for 1 hr. The crystals were collected by filtration and washed with acetonitrile (2 L). Acetonitrile (14 L) was again charged to the wet crystals, and the mixture was stirred under reflux for 2 hrs. The mixture was allowed to return to room temperature and stirred for 1 hr. The crystals were collected by filtration and washed with acetonitrile (1.1 L). After drying in vacuo at 50° C., acetone (35.4 L) and water (8.85 L) were added, and the mixture was heated for dissolution. The mixture was gradually cooled until the crystals started to precipitate and aged while retaining the temperature for 1.5 hrs. The mixture was cooled under ice-cooling for 1.5 hrs. The crystals were collected by filtration, washed with ice-cooled acetonewater (1:2) (1.8 L) and dried in vacuo at 50° C. to give the title compound (1221.7 g, yield 63.5%) as white crystals.

$^1$H-NMR (300 MHz, CDCl$_3$)δ: 1.22–1.26 (2H, m), 1.56–1.69 (7H, m), 1.78–1.91 (4H, m), 2.24–2.29 (3H, m), 2.56–2.58 (4H, m), 2.73 (3H, s), 2.79–2.82 (2H, m), 3.62–3.74 (4H, m), 7.00–7.74 (7H, m).

Reference Example 10

1-Acetyl-4-piperidinecarboxylic acid

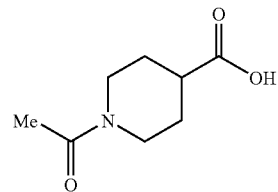

Isonipecotic acid (129.2 g, 1.00 mol) was dissolved in water (390 mL), and acetic anhydride (153.1 g, 1.50 mol) was added dropwise under ice-cooling for about 10 min. (dropwise addition at 15–18° C. for about 10 min.). After stirring at 55±5° C. for 2 hrs., the mixture was allowed to cool to room temperature and stirred under ice-cooling for 1 hr. The precipitated crystals were collected by filtration, washed with cold diisopropyl ether (125 mL×2) and dried under reduced pressure at 40° C. for 8 hrs. to give the title compound (129.1 g, yield 75.4%).

$^1$H-NMR (300 MHz, CDCl$_3$)δ: 4.40 (1H, dt, J=13.4 Hz), 3.79 (1H, dt, J=13.6 Hz), 3.17 (1H, dt, J=13.9 Hz), 2.87 (1H, dt, J=Hz), 2.62–2.55 (3H, s), 2.01–1.94 (2H, m), 1.75–1.65 (2H, m)

Reference Example 11

1-Acetyl-4-piperidinecarbonyl chloride

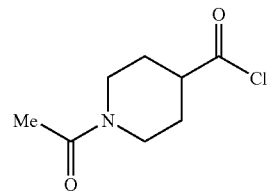

To thionyl chloride (685 mL) was added the compound (85.6 g, 0.50 mol) obtained in Reference Example 10, and the mixture was stirred at room temperature for 2 hrs. The precipitated crystals were collected by filtration, washed with diisopropyl ether (250 mL×2) and dried under reduced pressure at 30° C. for 8 hrs. to give the title compound (84.4 g, yield:89.0%).

$^1$H-NMR (300 MHz, CDCl$_3$)δ: 1.70–1.90 (2H, m), 2.05–2.26 (2H, m), 2.26 (3H, s), 2.90–3.25 (4H, m), 3.95–4.30 (2H, br), exchange proton in the range of about 3.5–4.5 ppm (2H, br)

Reference Example 12

3-Chloro-N-(3-chloropropyl)-4-methylaniline hydrochloride

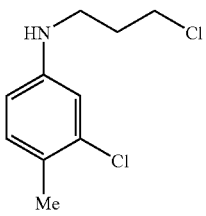

3-Chloro-4-methylaniline (10.0 g, 70.6 mmol), 1-bromo-3-chloropropane (34.7 mL, 55.6 g, 353 mmol) and triethylamine (21.4 g, 212 mmol) were charged. The mixture was stirred at 25–28° C. for 24 hrs. Water (50 mL) and methyl ethyl ketone (25 mL) were added for partitioning. The organic layer was washed twice with water (50 mL). Conc. hydrochloric acid (35 mL, 5.7 eq) was dropwise added to the organic layer under ice-cooling. The mixture was stirred at room temperature for 1 hr. The crystals were collected by filtration, washed with diisopropyl ether (10 mL) and dried in vacuo at 50° C. to give the title compound (14.12 g, yield 78.5%) as pale-yellow crystals.

$^1$H-NMR (300 MHz, DMSO)δ: 2.11 (2H, quint, J=6.9 Hz), 2.28 (3H, s), 3.29 (2H, t, J=7.3 Hz), 3.76 (2H, t, J=6.5 Hz), 7.16–7.37 (3H, m).

Reference Example 13

1-Acetyl-N-(3-chloro-4-methylphenyl)-N-(3-chloropropyl)-4-piperidine carboxamide

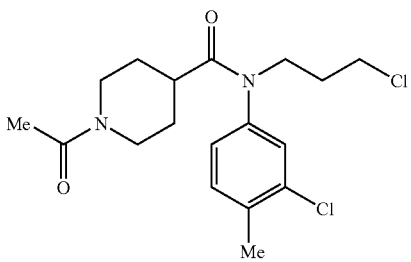

The compound (3.06 g, 12.0 mmol) obtained in Reference Example 12 and N-methylpyrrolidone (15 mL) were charged and, after dissolution, the compound (1.14 g, 6.00 mmol) obtained in Reference Example 11 was added 3 times every 30 min. (total 1.5 equivalents) to give a yellow suspension. The suspension was stirred at 20–26° C. for 1 hr., and water (45 mL) was added at 10–20° C. to once give a yellow solution, followed by precipitation of a small amount of an oil. A seed crystal was added, and the crystals were gradually precipitated. After stirring at 20–26° C. for 2 hrs., the crystals were collected by filtration, washed with water (6.0 mL) and dried to give the title compound (3.88 g, yield 87.1%) as white crystals.

$^1$H-NMR (300 MHZ, CDCl$_3$)δ: 1.61–1.77 (4H, m), 1.96–2.05 (5H, m), 2.33–2.44 (5H, m), 2.84–2.90 (1H, m), 3.51–3.56 (2H, t), 3.74–3.80 (3H, m), 4.49–4.54 (1H, d), 6.96–7.33 (3H, m).

Reference Example 14

1-Acetyl-N-[3-[4-(4-carbamoylbenzyl)-1-piperidyl] propyl]-N-(3-chloro-4-methylphenyl)-4-piperidine carboxamide

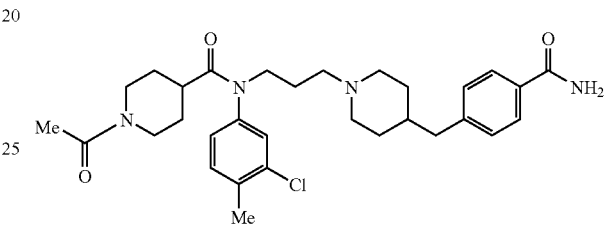

The compound (1.11 g, 3.00 mmol) obtained in Reference Example 13, the compound (0.720 g, 3.30 mmol) obtained in Example 5, N,N-dimethylformamide (5.5 mL) and acetonitrile (5.5 mL) were charged, and potassium carbonate (1.66 g, 12.0 mmol) and potassium iodide (0.598 g, 3.60 mmol) were successively added thereto to give a white suspension. The suspension was stirred at 70–75° C. for 2 hrs., and water (22 mL) was dropwise added at 20–25° C. The mixture was extracted with ethyl acetate (11 mL×2) and washed with brine (saturated brine 3 mL+water 8 mL), which was followed by solvent substitution with acetonitrile (11 mL) to allow precipitation of crystals. The mixture was stirred at 20–25° C. for 1 hr. and at 0–5° C. for 1 hr., then the crystals were collected by filtration, washed with acetonitrile (1 mL×2) and dried to give the title compound (1.00 g, yield 60.3%) as white crystals.

$^1$H-NMR (300 MHz, CDCl$_3$)δ: 1.23–1.28 (2H, m), 1.55–1.89 (11H, m), 2.04 (3H, s), 2.23–2.42 (7H, m), 2.55–2.58 (2H, m), 2.80–2.84 (3H, m), 3.61–3.67 (2H, t), 3.73–3.78 (1H, m), 4.47–4.53 (1H, m), 6.00 (2H, br.s, NH$_2$), 6.94–7.74 (7H, m).

Example 7

Production of 4-(4-piperidylidenemethyl)benzamide

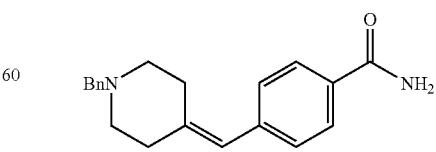

The compound (0.50 g, 1.84 mmol) obtained in Example 2, 1-benzyl-4-piperidone (418 mg, 2.21 mmol, 1.2 eq) and N,N-dimethylformamide (3.5 ml) were charged, and the mixture was stirred under ice-cooling. Potassium t-butoxide (455 mg, 4.06 mmol, 2.2 eq) was added, and the mixture was stirred at room temperature for 4 hrs. Water (10 ml) was dropwise added under ice-cooling, and the mixture was stirred for 1 hr. The crystals were collected by filtration, washed with water (3 ml) and dried in vacuo at 50° C. to give the title compound (453 mg, yield 79.9%) as slightly yellow crystals.

¹H-NMR (300 MHz, CDCl₃)δ: 2.40–2.57 (8H, m), 3.54 (2H, s), 6.04 (2H, br.s, NH₂), 6.29 (1H, s), 7.25–7.77 (9H, m).

Reference Example 15

Production of 1-acetyl-4-piperidinecarboxylic acid

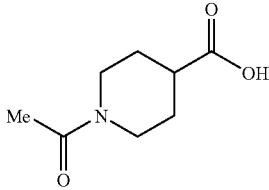

Isonipecotic acid (10.0 g, 0.078 mol) and ethyl acetate (30.0 ml) were charged at room temperature. Acetic anhydride (11.9 g, 1.50 eq) was dropwise added over about 10 min. while retaining not more than 20° C. After stirring at 55±5° C. for 2 hrs., the mixture was allowed to cool to room temperature over 1 hr., ice-cooled and stirred at not higher than 10° C. for 1 hr. The precipitated crystals were collected by filtration and washed with diisopropyl ether (10 ml×2) and dried in vacuo at 50° C. to give the title compound (11.9 g, yield 89.8%) as white crystals.

¹H-NMR (300 MHz, DMSO) δ: 1.32–1.51 (2H, m), 1.76–1.84 (2H, m), 1.98 (3H, s), 2.43–2.50 (1H, m), 2.65–2.68 (1H, m), 3.04–3.12 (1H, m), 3.71–3.75 (1H, m), 4.16–4.20 (1H, m).

Example 8

Production of 1-acetyl-N-(3-chloro-4-methylphenyl)-N-(3-chloropropyl)-4-piperidine carboxamide

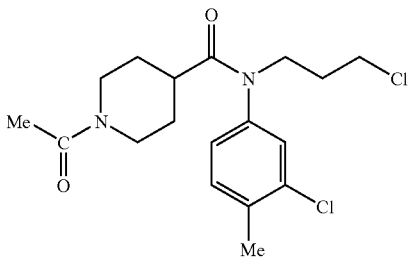

The compound (863 g, 5.04 mol, 1.2 eq) obtained in Reference Example 10 and N-methylpyrrolidone (6.4 L) were charged, and the mixture was stirred at room temperature for dissolution. Thionyl chloride (600 g, 5.04 mol, 1.2 eq) was dropwise added under ice-cooling (inner temperature 4–12° C.), and the mixture was stirred under ice-cooling for 1 hr. Thereto was added compound (1069 g, 4.20 mol) obtained in Reference Example 12, and the mixture was stirred at room temperature for 2 hrs. The reaction mixture was poured into iced water (12.8 L). A seed crystal was added, and the mixture was stirred at room temperature. After precipitation of crystals, water (6.4 L) was added dropwise, and the mixture was stirred overnight at room temperature. The mixture was stirred under ice-cooling for 2 hrs. The crystals were collected by filtration, washed with water (5 L) and dried in vacuo at 50° C. to give the title compound (1350 g, yield 86.6%) as white crystals.

¹H-NMR (300 MHz, CDCl₃)δ: 1.61–1.80 (4H, m), 1.96–2.03 (2H, m), 2.05 (3H, s), 2.33–2.39 (2H, m), 2.43 (3H, s), 3.53 (2H, t, J=6.6 Hz), 3.75–3.80 (3H, m), 4.49–4.53 (1H, m),6.96–7.33 (3H, m).

Example 9

1-Acetyl-N-[3-[4-(4-carbamoylbenzyl)-1-piperidyl]propyl]-N-(3-chloro-4-methylphenyl)-4-piperidine carboxamide

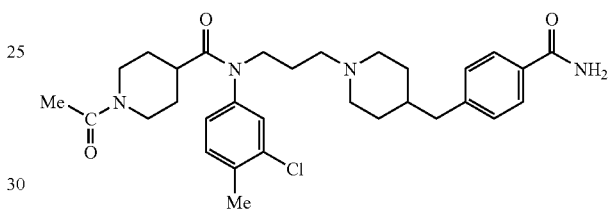

The compound (1237.0 g, 3.332 mol) obtained in Example 8, potassium iodide (608.3 g, 3.665 mol, 1.1 eq), anhydrous potassium carbonate (1381.4 g, 9.995 mol, 3.0 eq), the compound (800.0 g, 3.665 mol, 1.1 eq) obtained in Example 4 and acetonitrile (12.37 L) were charged, and the mixture was stirred under reflux (81–82° C.) for 4 hrs. The mixture was allowed to return to room temperature, and added to cold water (24.74 L), to which ethyl acetate (12.37 L) was added for partitioning. The organic layer was washed with 10% aqueous sodium chloride solution (24.74 L). Magnesium sulfate was added to the organic layer at not higher than 20° C., and after stirring for 10 min., filtered off. The organic layer was concentrated under reduced pressure and acetonitrile (1.24 L) was added to the concentrated residue. The mixture was heated for dissolution. The mixture was cooled to room temperature, and a seed crystal was added. t-Butyl methyl ether (3.50 L) was added, and the mixture was stirred overnight at room temperature. Because the crystals did not precipitate, t-butyl methyl ether (1.00 L) was added dropwise, and the mixture was stirred overnight at room temperature. After confirmation of precipitation, t-butyl methyl ether (6.50 L) was added, and the mixture was ice-cooled and aged at not higher than 10° C. for 1.5 hrs. The crystals were collected by filtration and washed with acetonitrile-t-butyl methyl ether (0.1:1.9) (2.47 L). The obtained crystals were suspended in pure water (12.37 L), and the suspension was stirred at room temperature for 1 hr. The crystals were collected by filtration, washed with pure water (3.71 L) and dried in vacuo at 50° C. to give the title compound as slightly yellow crystals (1216 g, yield 66.2%).

The obtained slightly yellow crystals (1196.0 g, 2.162 mol), acetone (2.99 L, 2.5 v/w) and pure water (5.98 L, 5.0 v/w) were charged. The mixture was heated to 60° C. for dissolution. The mixture was allowed to return to room temperature, a seed crystal was added, and the mixture was stirred overnight. After confirmation of precipitation, water (5.980 L, 5.0 v/w) was added, and the mixture was stirred at room temperature for 1 hr., and under ice-cooling for 1 hr. The crystals were collected by filtration, washed with water (2.00 L) and dried in vacuo at 50° C. to give the title compound as white crystals (1146.5 g, recovery 95.9%). The obtained white crystals (1076.0 g), ethanol (1.00 L) and ethyl acetate (2.00 L) were charged, and the mixture was heated for dissolution. After confirmation of dissolution, the mixture was dust-removed by filtration, and washed with ethanol (76 ml) and ethyl acetate (152 ml). The temperature was raised, and dissolution was confirmed under reflux. t-Butyl methyl ether (2.15 L) and a seed crystal (0.5 g) were successively added, and after heating under reflux for 1 hr., the mixture was gradually cooled and stirred overnight at room temperature. After confirmation of precipitation, t-butyl methyl ether (4.30 L) was added dropwise, and the mixture was stirred at room temperature for 1 hr. and under ice-cooling for 1 hr. The crystals were collected by filtration, washed with t-butyl methyl ether (2.15 L) and dried in vacuo at 50° C. to give the title compound (1007 g, recovery 93.6%).

$^1$H-NMR (300 MHz, CDCl$_3$)δ: 1.19–1.27 (2H, m), 1.56–2.00 (11H, m), 2.04 (3H, s), 2.24–2.39 (4H, m), 2.42 (3H, s), 2.55–2.57 (2H, m), 2.80–2.88 (3H, m), 3.61–3.78 (3H, m), 4.48–4.52 (1H, m), 6.94–7.74 (7H, m).

Example 10

1-Acetyl-N-[3-[4-(4-carbamoylbenzyl)-1-piperidyl] propyl]-N-(3-chloro-4-methylphenyl)-4-piperidine carboxamide

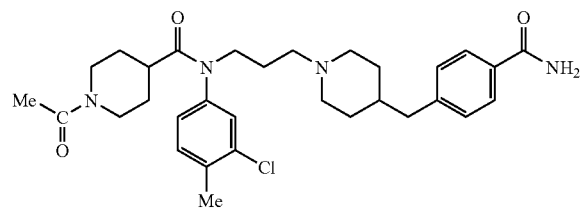

The compound (7.43 g, 20.0 mmol) obtained in Example 8, the compound (4.80 g, 22.0 mmol) obtained in Example 4, anhydrous potassium carbonate (8.29 g, 60.0 mmol), potassium iodide (3.65 g, 22.0 mmol) and acetonitrile (74 ml) were charged, and the mixture was heated under reflux for 4 hrs. The mixture was allowed to return to room temperature, poured into water (150 ml) and extracted with ethyl acetate (74 ml). The organic layer was washed with 10% brine (150 ml), magnesium sulfate (7.4 g) was added, and the mixture was stirred for 10 min. Insoluble materials were filtered off, and the filtrate was washed with ethyl acetate (7.4 ml) and concentrated under reduced pressure until the filtrate became about 15 ml. Acetonitrile (7.4 ml), diisopropyl ether (22 ml) and a seed crystal were added, and the mixture was stirred overnight at room temperature to allow precipitation. Diisopropyl ether (22 ml) was added, and the mixture was stirred at room temperature for 30 min. and at 0–10° C. for 1 hr. Then the crystals were collected by filtration and washed with acetonitrile-diisopropyl ether (1:3 mixture, 14 ml). The obtained crystals were suspended in water (74 ml) by stirring, collected by filtration, washed with water (15 ml) and dried in vacuo at 50° C. to give the title compound as pale-brown crystals (7.4 g, yield 66.9%).

Acetone (18.5 ml) and water (37.0 ml) were added to the obtained pale-brown crystals (7.4 g), and the mixture was dissolved by heating. A seed crystal was added at 20–30° C., and the mixture was stirred overnight at room temperature to allow precipitation. When water (37.0 ml) was added, an oily substance floated, and when stirred at room temperature for 1.5 hrs., crystallization occurred. The mixture was stirred at room temperature for 1 hr. and at 0–10° C. for 1 hr. The crystals were collected by filtration, washed with water (15 ml) and dried in vacuo at 50° C. to give the title compound as slightly brown crystals (6.86 g, recovery 92.7%).

The obtained slightly brown crystals (10.0 g), ethanol (10.0 ml) and ethyl acetate (10.0 ml) were charged, and the mixture was heated for dissolution (ca. 70° C.). After confirmation of dissolution, and the mixture was gradually cooled. Diisopropyl ether (10.0 ml) and a seed crystal were successively added at about 60° C., and the mixture was stirred overnight at about 50° C. After confirmation of precipitation, diisopropyl ether (40.0 ml) was added dropwise over 30 min., and the mixture was stirred overnight at room temperature. The mixture was stirred under ice-cooling for 1 hr., and the crystals were collected by filtration, washed with a mixture of diisopropyl ether (10.0 ml) and ethyl acetate (2.0 ml) and dried in vacuo at 50° C. to give the title compound (8.54 g, recovery 85.4%) as nearly white crystals.

$^1$H-NMR (300 MHz, CDCl$_3$)δ: 1.19–1.27 (2H, m), 1.56–2.00 (11H, m), 2.04 (3H, s), 2.24–2.39 (4H, m), 2.42 (3H, s), 2.55–2.57 (2H, m), 2.80–2.88 (3H, m), 3.61–3.78 (3H, m), 4.48–4.52 (1H, m), 6.94–7.74 (7H, m).

Example 11

1-Acetyl-N-[3-[4-(4-carbamoylbenzyl)-1-piperidyl] propyl]-N-(3-chloro-4-methylphenyl)-4-piperidine carboxamide

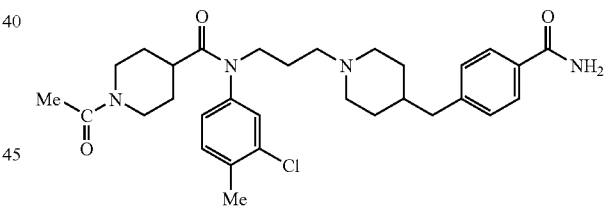

The compound (18.6 g, 50.0 mmol) obtained in Example 8, the compound (12.0 g, 55.0 mmol) obtained in Example 4, anhydrous potassium carbonate (20.7 g, 150 mmol), potassium iodide (9.13 g, 55.0 mmol) and acetonitrile (186 ml) were charged, and the mixture was heated under reflux for 5 hrs. The mixture was allowed to return to room temperature, poured into water (372 ml) and extracted with ethyl acetate (186 ml). The organic layer was washed with 10% brine (372 ml). Magnesium sulfate (18.6 g) was added, and the mixture was stirred for 10 min. Insoluble materials were filtered off, and the filtrate was washed with ethyl acetate (18.6 ml) and concentrated under reduced pressure until the filtrate became about 37 ml. Acetonitrile (18.3 ml), heptane (18.0 ml), ethyl acetate (18.6 ml) and a seed crystal were added, and the mixture was stirred at room temperature for 1 hr. to allow precipitation. Heptane (28.0 ml) and ethyl acetate (28.0 ml) were added, and the mixture was stirred at room temperature overnight, and at 0–5° C. for 1 hr. The crystals were collected by filtration and washed with ethyl acetate-heptane (1:2 mixture, 18.6 ml). The obtained crystals were suspended in water (186 ml) by stirring, collected by filtration, washed with water (18.6 ml) and dried in vacuo at 50° C. to give the title compound as nearly white crystals (17.2 g, yield 62.2%).

Acetone (40.5 ml) and water (81.0 ml) were added to the obtained nearly white crystals (16.2 g), and the mixture was heated for dissolution. A seed crystal was added at 20–30° C., and the mixture was stirred at room temperature overnight to allow precipitation. Water (81.0 ml) was added, and the mixture was stirred at room temperature for 2 hrs. and at 0–5° C. for 1 hr. The crystals were collected by filtration, washed with water (16 ml) and dried in vacuo at 50° C. to give the title compound as nearly white crystals (15.4 g, recovery 95.1%).

Ethanol (12.0 ml) and ethyl acetate (12.0 ml) were added to the obtained nearly white crystals (15.0 g), and the mixture was heated for dissolution, filtrated while hot and washed with ethanol-ethyl acetate (1:1 mixture, 6.0 ml). Heptane (15.0 ml) and a seed crystal were added at 40–50° C., and the mixture was stirred at 40–50° C. for 17 hrs. The mixture was gradually cooled and stirred at room temperature for 1 hr. Heptane (60.0 ml) was added dropwise over 30 min. The mixture was stirred at room temperature for 3 hrs. and at 0–5° C. for 1 hr. The crystals were collected by filtration, washed with heptane-ethyl acetate (5:1 mixture, 18.0 ml) and dried in vacuo at 50° C. to give the title compound (13.9 g, recovery 92.7%) as nearly white crystals.

$^1$H-NMR (300 MHz, CDCl$_3$)δ1.19–1.27 (2H, m), 1.56–2.00 (11H, m), 2.04 (3H, s), 2.24–2.39 (4H, m), 2.42 (3H, s), 2.55–2.57 (2H, m), 2.80–2.88 (3H, m), 3.61–3.78 (3H, m), 4.48–4.52 (1H, m), 6.94–7.74 (7H, m).

INDUSTRIAL APPLICABILITY

According to the method of the present invention, benzylpiperidine compounds useful as synthesis starting materials of pharmaceutical agents, agricultural chemicals and the like can be produced conveniently by a short step.

This application is based on a patent application Ser. No. 2001-010354 filed in Japan, the contents of which are hereby incorporated by reference.

The invention claimed is:

1. A process for the preparation of a compound represented by the formula:

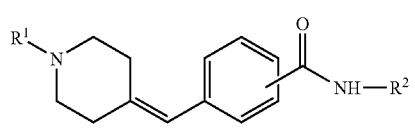

(III)

wherein
R$^1$ is a hydrogen atom or an amino-protecting group and
R$^2$ is a hydrogen atom, a hydrocarbon group optionally having substituents, an alkoxy group optionally having substituents or a heterocyclic group optionally having substituents, or a salt thereof, which comprises reacting a compound represented by the formula:

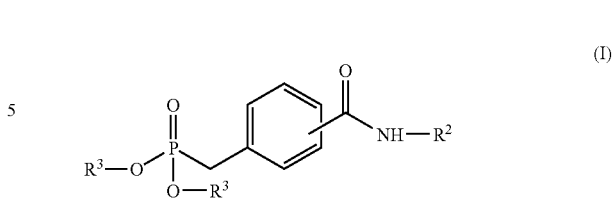

(I)

wherein R$^3$ is a lower alkyl group and R$^2$ is as defined above, or a salt thereof, with a compound represented by the formula:

(II)

wherein R$^1$ is as defined above, or a salt thereof.

2. A process for the preparation of a compound represented by the formula:

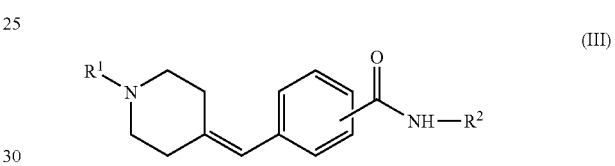

(III)

wherein
R$^1$ is a hydrogen atom or an amino-protecting group and
R$^2$ is a hydrogen atom, a hydrocarbon group optionally having substituents, an alkoxy group optionally having substituents or a heterocyclic group optionally having substituents, or a salt thereof, which comprises reacting a compound represented by the formula:

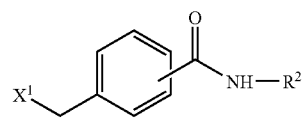

(IV)

wherein X$^1$ is a halogen atom and R$^2$ is as defined above, or a salt thereof, with a trialkyl phosphite represented by the formula:

(R$^3$O)$_3$P (V)

wherein R$^3$ is a lower alkyl group, and thereafter reacting with a compound represented by the formula:

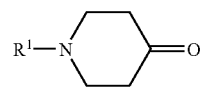

(II)

wherein R$^1$ is as defined above, or a salt thereof.

3. The process of claim 2, wherein the compound represented by the formula (IV) or a salt thereof is reacted with the trialkyl phosphite represented by the formula (V) to give a compound represented by the formula:

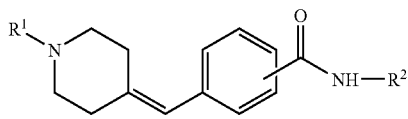

(III)

wherein
R² is a hydrogen atom, a hydrocarbon group optionally having substituents, an alkoxy group optionally having substituents or a heterocyclic group optionally having substituents, and
R³ is a lower alkyl group,
or a salt thereof.

4. A process for the preparation of a compound represented by the formula:

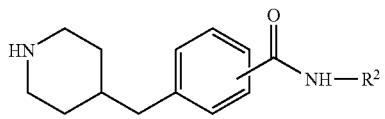

(VIII′)

wherein
R² is a hydrogen atom, a hydrocarbon group optionally having substituents, an alkoxy group optionally having substituents or a heterocyclic group optionally having substituents,
or a salt thereof, which comprises:
reacting a compound represented by the formula:

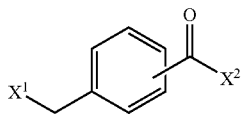

(VI)

wherein X¹ is a halogen atom and X² is a leaving group, with a compound represented by the formula:

R²NH₂ (VII)

wherein R² is as defined above, or a salt thereof, to give a compound represented by the formula:

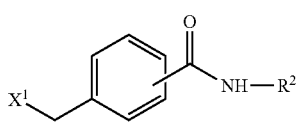

(IV)

wherein R² and X¹ are as defined above, or a salt thereof;
reacting the compound represented by the formula (IV) or a salt thereof with a trialkyl phosphite represented by the formula:

(R³O)₃P (V)

wherein R³ is a lower alkyl group;
thereafter reacting with a compound represented by the formula:

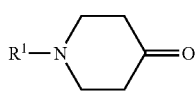

(II)

wherein R¹ is a hydrogen atom or an amino-protecting group, or a salt thereof, to give a compound represented by the formula:

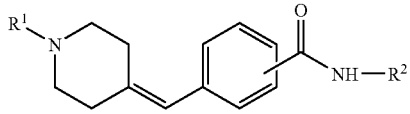

(III)

wherein R¹ and R² are as defined above, or a salt thereof; and
reducing and thereafter where necessary deprotecting the compound represented by the formula(III) or a salt thereof.

5. The process of claim 4 which comprises:
reacting a compound represented by the formula:

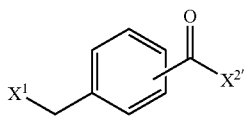

(VI′)

wherein X¹ and X²′ are each a halogen atom, with a compound represented by the formula:

R²NH₂ (VII)

wherein R² is a hydrogen atom, a hydrocarbon group optionally having substituents, an alkoxy group optionally having substituents or a heterocyclic group optionally having substituents, or a salt thereof, to give a compound represented by the formula:

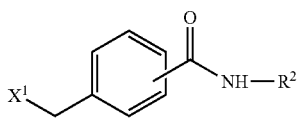

(IV)

wherein R² and X¹ are as defined above, or a salt thereof;
reacting the compound represented by the formula (IV) or a salt thereof with a trialkyl phosphite represented by the formula:

(R³O)₃P (V)

wherein R³ is a lower alkyl group, to give a compound represented by the formula:

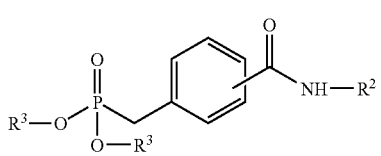

(I)

wherein R² and R³ are as defined above, or a salt thereof;
reacting the compound represented by the formula (I) or a salt thereof with a compound represented by the formula:

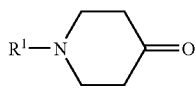
(II)

wherein R¹ is a hydrogen atom or an amino-protecting group, or a salt thereof, to give a compound represented by the formula:

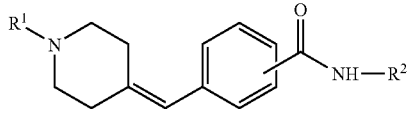
(III)

wherein R¹ and R² are as defined above, or a salt thereof; and reducing and thereafter where necessary deprotecting the compound represented by formula (III) or a salt thereof.

6. The process of claim 1 wherein the compound represented by the formula (II) or a salt thereof is reacted in the presence of a base.

7. The process of claim 6, wherein the base is t-butoxide of an alkali metal.

8. The process of claim 7, wherein the base is potassium t-butoxide.

9. A compound represented by the formula:

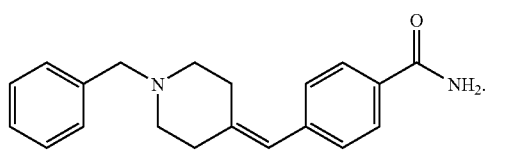
(III')

10. The process of claim 2, wherein the compound represented by the formula (IV) or a salt thereof is reacted with the compound represented by the formula (V) in the presence of alkali metal iodide.

11. The process of claim 2, wherein the compound represented by the formula (II) or a salt thereof is reacted in the presence of a base.

12. The process of claim 4, wherein the compound represented by the formula (IV) or a salt thereof is reacted with the compound represented by the formula (V) in the presence of alkali metal iodide.

13. The process of claim 4, wherein the compound represented by the formula (II) or a salt thereof is reacted in the presence of a base.

* * * * *